United States Patent [19]

Tatsuoka et al.

[11] Patent Number: 4,845,094

[45] Date of Patent: Jul. 4, 1989

[54] 2-PHENYLBENZOXEPIN DERIVATIVE

[75] Inventors: Toshio Tatsuoka, Nishinomiya; Kayoko Nomura, Takatsuki; Fumio Satoh, Nagaokakyo; Takafumi Ishihara, Toyonaka; Seiji Miyano, Fukuoka; Kunihiro Sumoto, Oonojo, all of Japan

[73] Assignee: Suntory Limited, Osaka, Japan

[21] Appl. No.: 63,839

[22] Filed: Jun. 19, 1987

[30] Foreign Application Priority Data

Jun. 20, 1986 [JP] Japan .................. 61-142898

[51] Int. Cl.$^4$ ............ C07D 313/00; A61K 31/33
[52] U.S. Cl. .................. 514/228.2; 514/450; 514/444; 514/422; 514/337; 514/320; 514/256; 514/255; 514/233.5; 549/355; 549/60; 548/525; 546/269; 546/196; 544/376; 544/335; 544/334; 544/333; 544/147; 544/62
[58] Field of Search ............ 549/355, 60; 548/525; 546/269, 196; 544/376, 335, 334, 333, 147, 62; 514/450, 444, 228.2, 233.5, 255, 256, 320, 337, 422

[56] References Cited

U.S. PATENT DOCUMENTS

| 4,279,904 | 7/1981 | Ohlendorf et al. ......... 548/215 |
| 4,736,031 | 4/1988 | Sugihara et al. ......... 549/355 |

FOREIGN PATENT DOCUMENTS

| 0024560 | 11/1981 | European Pat. Off. . |
| 0180890 | 5/1986 | European Pat. Off. . |
| 1593760 | 6/1972 | Fed. Rep. of Germany . |
| 1211258 | 11/1970 | United Kingdom . |

Primary Examiner—Nicky Chan
Attorney, Agent, or Firm—Burns, Doane, Swecker & Mathis

[57] ABSTRACT 2-phenylbenzoxepin derivatives having a hypoglycemic activity, hypotensive activity, and platelet coagulation inhibiting activity, a process for production of the derivatives, and pharmaceutical compositions containing the derivatives.

3 Claims, No Drawings

2-PHENYLBENZOXEPIN DERIVATIVE

BACKGROUND OF THE INVENTION

1. Field of the Invention

The present invention relates to new 2-phenylbenzoxepin derivatives and a process for production thereof, and to a pharmaceutical composition containing the derivatives.

2. Description of the Related Art

Diabetes is classified into two types: type I, an insulin-dependent type, and type II, a non-insulin-dependent type. In the therapy of type II diabetes, which is suffered by more than 90% of all diabetics, in addition to the dietary regimen which is a major method of curing diabetes, sulfonylurea compounds, sulfonylamide compounds and biguanide compounds are used as therapeutic agents for alleviating diabetes. However, a long-term internal administration of these agents may cause various side effects, such as hepatic disorders, severe hypotension, and the like.

SUMMARY OF THE INVENTION

Accordingly, the present invention provides new 2-phenylbenzoxepin derivatives exhibiting an excellent hypoglycemic activity, platelet coagulation-inhibiting action, and hypotensive activity.

More specifically, the present invention provides a 2-phenylbenzoxepin derivative represented by the following general formula (I):

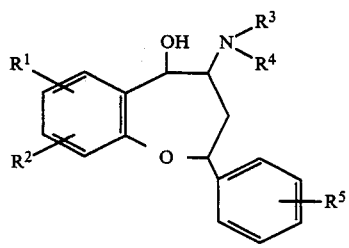
(I)

wherein $R^1$ and $R^2$ independently represent a hydrogen atom, halogen atom, hydroxyl group, methyl group or methoxy group;

$R^3$ and $R^4$ independently represent a hydrogen atom, lower alkyl group or the group $-(CH_2)_n-Y$, wherein n represents an integer of 1 to 5 and Y represents an optionally substituted aromatic group or heterocyclic group; or $R^3$ and $R^4$, together with a nitrogen atom to which they are bonded, form an optionally substituted heterocyclic group; and $R^5$ represents a hydrogen atom, halogen atom, optionally substituted alkyl group, hydroxymethyl group, or optionally esterified or amidated carboxyl group, and a pharmaceutically acceptable acid addition salt thereof.

The present invention also provides a pharmaceutical composition comprising a 2-phenylbenzoxepin derivative or pharmaceutically acceptable acid addition salt thereof, and a pharmaceutically acceptable carrier.

Moreover, the present invention provides a process for the production of the above-mentioned 2-phenylbenzoxepin derivatives and a pharmaceutically acceptable acid addition salt thereof, comprising the steps of:

(a) reducing a compound represented by the following formula (VI):

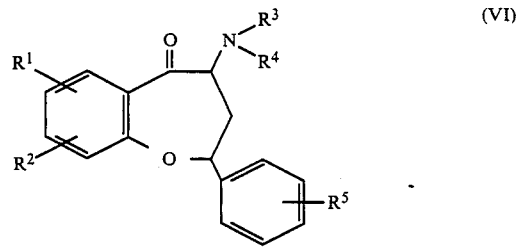
(VI)

wherein $R^1$, $R^2$, $R^3$, $R^4$ and $R^5$ have the same meanings as defined above; or (b) for production of a compound of the formula (I) wherein $R^3$ and $R^4$ represent a hydrogen atom, reducing an oxime represented by the following formula (VII):

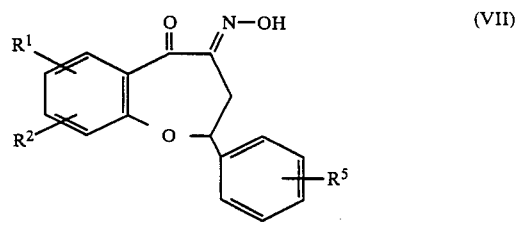
(VII)

wherein $R^1$, $R^2$ and $R^5$ have the same meanings as defined above, and if necessary, hydrolyzing the reduced product; or (c) for production of a compound of the formula (I) wherein $R^3$ represents a hydrogen atom and $R^4$ represents the group $-(CH_2)_n-Y$ wherein n and Y have the same meanings as defined above, reacting a compound of the formula (I) wherein $R^3$ and $R^4$ represent a hydrogen atom with a halogen compound represented the formula (VIII):

$$X-(CH_2)_n-Y \qquad (VIII)$$

wherein X represents a halogen atom and n and Y have the same meanings as defined above; or (d) for production of a compound of the formula (I) wherein $R^3$ represents a hydrogen atom and $R^4$ represents the group $-(CH_2)_n-Y$ wherein n and Y have the same meanings as defined above, reacting a compound of the formula (I) wherein $R^3$ and $R^4$ represent a hydrogen atom with a halogen compound represented by the formula (VIII'):

$$X-CO-(CH_2)_{n-1}-Y \qquad (VIII')$$

wherein X represents a halogen atom and n and Y have the same meanings as defined above, and reducing the product; or (e) for production of a compound of the formula (I) wherein $R^3$ represents a methyl group and $R^4$ represents the group $-(CH_2)_n-Y$, wherein n and Y have the same meanings as defined above, reducing a compound represented by the following formula (X):

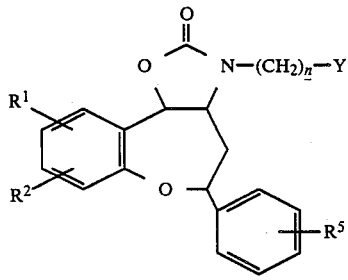

wherein $R^1$, $R^2$, $R^5$, n, and Y have the same meanings as defined above; and optionally (f) converting the resulting compound to salts, or a resulting salt to other salts, or a free compound.

DESCRIPTION OF THE PREFERRED EMBODIMENT

In the definitions in the general formula (I) to (X), halogen includes fluorine, chlorine, bromine, and iodine.

The lower alkyl group preferably includes an alkyl group having 1 to 6 carbon atoms, such as methyl, ethyl, n-propyl, isopropyl, n-butyl, isobutyl, tert-butyl, pentyl, hexyl groups, and the like.

The aromatic group as Y in the substituent groups $R^3$ and $R^4$ is, for example, phenyl, tolyl, xylyl, anisoyl, dimethoxylphenyl, trimethoxylphenyl, chlorophenyl, hydroxyphenyl, dihydroxyphenyl, alkyloxycarbonylphenyl, hydroxymethylphenyl, halogenophenyl, or halogenomethylphenyl.

The heterocyclic group as Y in the substituent groups $R^3$ and $R^4$ is, for example, pyridyl, pyrimidyl, furyl, or thenyl.

The unsubstituted or substituted heterocyclic ring formed by $R^3$ and $R^4$, as well as a nitrogen atom to which $R^3$ and $R^4$ is bonded is, for example, a pyrolidine ring, piperidine ring, piperazine ring, morpholine ring, or thiomorpholine ring.

The optionally substituted alkyl group $R^5$ is, for example, halogenoalkyl, $C_1 \sim C_6$ straight, branched or cyclic alkyl.

The compound of the present invention represented by the general formula (I) can be produced by various processes.

For example, a known oxabicyclopentane derivative represented by the general formula (II):

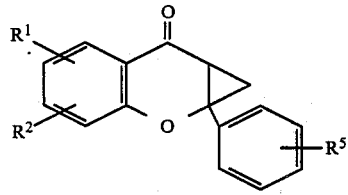

wherein $R^1$, $R^2$ and $R^3$ represent a hydrogen atom (P. Bennett, et al., *J. Chem. Soc.* Parkin Trans. I, (12), 2990 (1979), or a compound of the formula (II) wherein $R^1$, $R^2$ and $R^5$ have the same meanings as defined above, which compound can be synthesized according to the same procedure as described in *J. Chem. Soc.*, supra, is dissolved in an inert solvent such as benzene and then reacted with tri-n-butyltin hydride and azobisisobutylonitrile to form an benzoxepin derivative represented by the general formula (III):

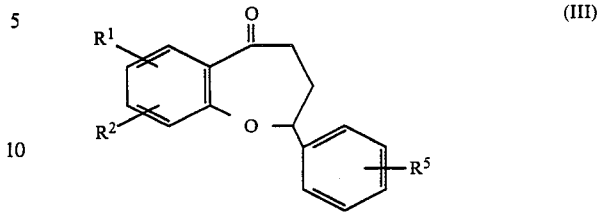

wherein $R^1$, $R^2$ and $R^5$ have the same meanings as defined above.

The compound of the formula (III) is then dissolved in an inert solvent, for example, an ether such as diethyl ether, and reacted with bromine to form a compound represented by the general formula (IV):

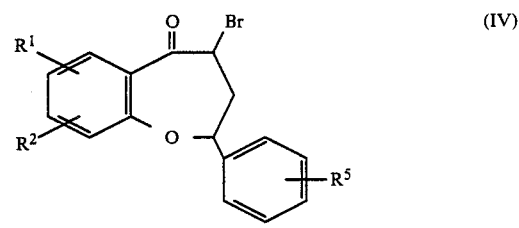

wherein $R^1$, $R^2$ and $R^5$ have the same meanings as defined above.

Next, the bromide compound of the formula (IV) is reacted with an amine represented by the general formula (V):

wherein $R^3$ and $R^4$, have the same meanings as defined above, to form a compound represented by the general formula (VI):

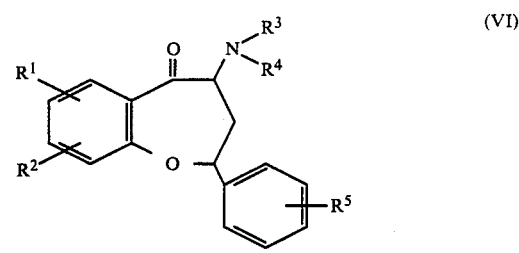

wherein $R^1$, $R^2$, $R^3$, $R^4$ and $R^5$ have the same meanings as described above. In this reaction, an inert solvent such as benzene, methanol or the like can be used as a reaction medium.

Finally, the compound of the formula (VI) is reduced with a conventional reducing agent, such as sodium borohydride, in a appropriate inert solvent such as tetrahydrofuran or methanol, to obtain a compound of the present invention represented by the general formula (Ia):

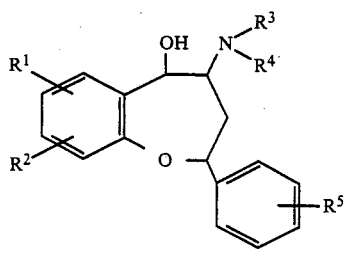

(Ia)

wherein $R^1$, $R^2$, $R^3$, $R^4$ and $R^5$ have the same meanings as described above.

Alternatively, the compound of the present invention can be synthesized as follows: An benzoxepin derivative represented by the general formula (III) is reacted with sodium butylnitrite in the presence of hydrogen chloride, in an appropriate inert solvent such as methylene chloride, tetrahydrofuran, or an ether such as diethyl ether, to form an oxime represented by the general formula (VII):

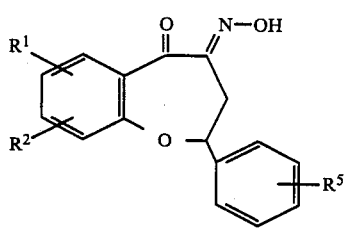

(VII)

wherein $R^1$, $R^2$ and $R^5$ have the same meanings as defined above. Finally, the oxime of the formula (VII) is reduced with lithium aluminium hydride in an appropriate inert solvent such as tetrahydrofuran to obtain a compound of the present invention represented by the general formula (Ib):

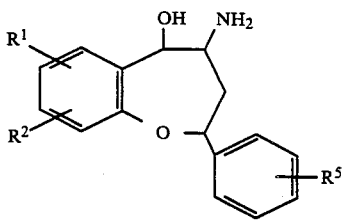

(Ib)

wherein $R^1$, $R^2$ and $R^5$ have the same meanings as defined above, in a mixture of stereoisomers.

Alternatively, the compound of the general formula (Ib) can be obtained by reduction of the oxime of the general formula (VII) with zinc powders/acetic acid in acetic anhydride, followed by reduction of the reduced product with sodium borohydride and alkaline hydrolysis.

The compound of the general formula (Ib) can be separated into four stereoisomers, by an appropriate separation means such as silica gel chromatography.

The above-mentioned compound (Ib) can be converted to a compound of the present invention represented by the general formula (Ic):

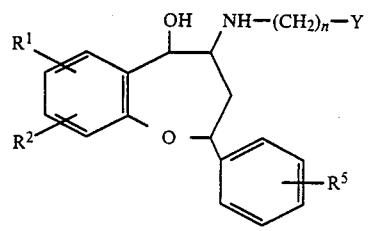

wherein $R^1$, $R^2$, $R^5$ and Y have the same meanings as defined above, by reacting the compound (Ib) with a halogen compound represented by the general formula (VIII):

$$X-(CH_2)_n-Y \quad (VIII)$$

wherein X represents a halogen atom, Y represents an optionally substituted aromatic or heterocyclic group, and n represents an integer of 1 to 5; or by reacting the compound (Ib) with a corresponding acid halide represented by the formula (VIII')

$$X-CO-(CH_2)_{n-1}-Y \quad (VIII')$$

and reduction of the resulting product with an appropriate reducing agent such as lithium aluminium hydride or diborane-THF complex.

Moreover, the above mentioned compound (Ib) can be converted to another compound of the present invention. For example, the compound (Ib) is reacted with carbonyl diimidazole to form an oxazolidin compound represented by the general formula (IX):

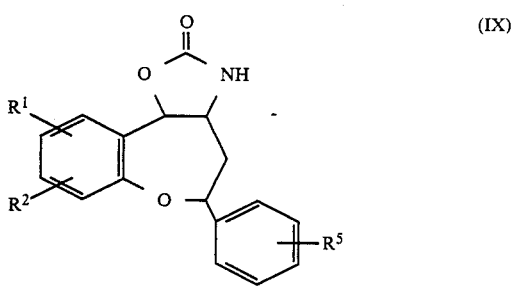

(IX)

wherein $R^1$, $R^2$, and $R^5$ have the same meanings as defined above; the compound (IX) is then reacted with the above-mentioned halogen compound (VIII) to form a compound represented by the general formula (X):

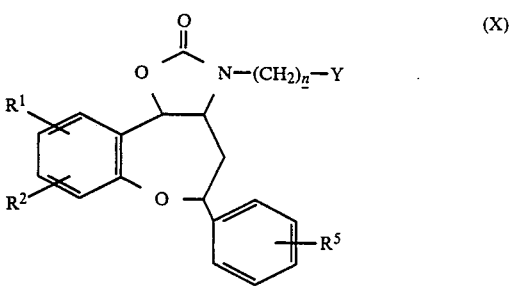

(X)

wherein $R^1$, $R^2$, $R^5$, n and Y have the same meanings as defined above; and the compound (X) is finally reduced with a reducing agent such as lithium aluminium hydride, to obtain a compound of the present invention represented by the general formula (Id);

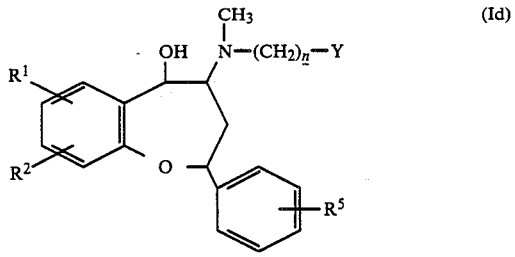

wherein $R^1$, $R^2$, $R^5$, n and Y have the same meanings as defined above.

The compound prepared as described above can be converted to corresponding acid addition salts, such as hydrochloride, maleate, fumarate, tartarate, by treating the compound with a corresponding acid according to a conventional procedure. Moreover, the resulting salt can be converted to a corresponding free compound by treating with alkaline solution according to a conventional procedure.

A mixture of stereoisomers of the present invention can be separated according to a conventional procedure such as column chromatography, for example, silica gel column chromatography.

Compounds of the general formula (I) of the present invention or pharmaceutically acceptable salts thereof may be administrated alone, or preferably, formulated to a desired formulation, by admixing with a pharmaceutically acceptable conventional carrier, excipient or diluent, and the formulation can be internally or parenterally administrated. The compound or formulation of the present invention is preferably internally administrated. The daily dose of the present compound is 0.1 mg to 100 mg/kg body weight, depending on, for example, the condition of the patient.

EXAMPLE

The present invention will now be further illustrated by, but is by no means limited to, the following examples.

Physico-chemical properties of compounds obtained in the examples are set forth in Table 1. In Table 1, $R^1$ to $R^5$ correspond to the substituents $R^1$ to $R^5$ in the general formula (I). Mixtures of stereoisomers were separated into individual isomers, and the physicochemical properties of the isomers were determined. In the Table, symbols a, b, c, and d attached to the compound numbers show different stereoisomers.

EXAMPLE 1

4-amino-5-hydroxy-2-phenyl-2,3,4,5-tetrahydro-1-benzoxepin (Compound Numbers 1a, 1b, 1c, and 1d)

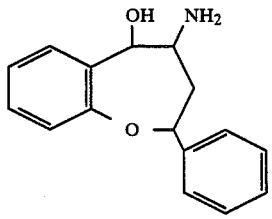

1.98 g (6.67 m moles) of 4-acetamido-5-hydroxy-2-phenyl-2,3,4,5-tetrahydro-1-benzoxepin (R4a; compoud of Reference Example 4) was dissolved in 60 ml of ethanol, 40 ml of 4N sodium hydroxide aqueous solution was added to the solution, and the whole was heated to reflux for 6 hours. After distilling off the methanol, water was added to the reaction mixture, which was then extracted with methylene chloride. The extract was washed with water, and dried with anhydrous magnesium sulfate. After filtrating off the magnesium sulfate, the filtrate was concentrated to obtain crude crystals, which were then recrystallized from a mixture of methanol, ethyl ether and hexane to obtain 1.33 g (yield 78.2%) of the compound according to this invention.

By the same procedure as described above, except that stereoisomers R4b and R4c of Reference Example 4 were used as the starting compound, stereoisomers 1b (yield 82.6%) and 1c (yield 83.4%) were obtained, respectively.

The titled compounds were also prepared according to the following process. 3.73 g (14.0 m moles) of 4-hydroxyimino-2-phenyl-2,3,4,5-tetrahydro-1-benzoxepin-5-one (compound of Reference Example 2) were dissolved in 200 ml of tetrahydrofurane, 2.12 g (55.8 m moles) of lithium aluminium hydride were added to the resulting solution, and the whole was heated to reflux for 7 hours and then cooled. A 3N sodium hydroxide aqueous solution was added to the reaction mixture to destroy the lithium aluminium hydride, and a supernatant was separated and dried with anhydrous magnesium sulfate. After filtrating off the magnesium sulfate, the resulting filtrate was concentrated to obtain a residue. The residue was applied to a silica gel column (300 g), and the column was eluted with a mixture of methylene chloride/methanol (90:10) to obtain stereoisomers 1a (344 mg; yield 9.5%), 1b (172 mg; yield 48%) 1c (211 mg; yield 5.9%), and 1d (703 mg; yield 19.7%) of the compound of this invention.

In the following Examples 2 to 9, the same procedure as described in Example 1 was repeated except that compounds of Reference Examples 5 to 12 were used as starting compounds to synthesize the compounds of this invention, respectively.

EXAMPLE 2

4-amino-5-hydroxy-7-methoxy-2-phenyl-2,3,4,5-tetrahydro-1-benzoxepin (Compounds 2a, 2b, and 2c)

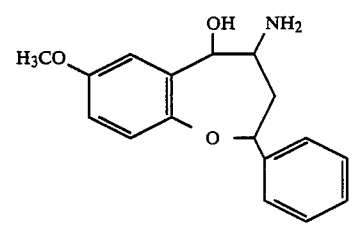

Compound 2a from compound R5a: yield 76.2%.
Compound 2b from compound R5b: 92.7%.
Compound 2c from compound R5c: 85.4%.

EXAMPLE 3

4-amino-5-hydroxy-8-methoxy-2-phenyl-2,3,4,5-tetrahydro-1-benzoxepin (Compounds 3a, 3b, and 3c)

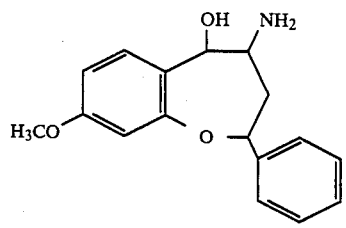

Compound 3a from compound R6a: 79.6%.
Compound 3b from compound R6b: 88.2%.
Compound 3c from compound R6c: 83.4%.

EXAMPLE 4

4-amino-5-hydroxy-8-chloro-2-phenyl-2,3,4,5-tetrahydro-1-benzoxepin (Compounds 4a, 4b, 4c and 4d)

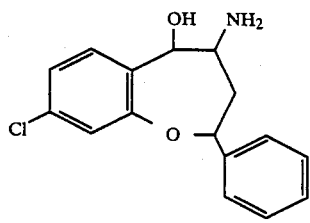

Compound 4a from compound R7a: 82.3%.
Compound 4b from compound R7b: 88.5%.
Compound 4c from compound R7c: 86.5%.
Compound 4d by a different process: 9.8%.

EXAMPLE 5

4-amino-5-hydroxy-7,8-dimethoxy-2-phenyl-2,3,4,5-tetrahydro-1benzoxepin (Compounds 5a, 5b, and 5c)

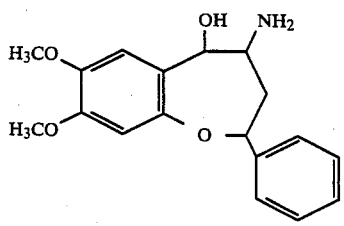

Compound 5a from compound R8a: 95.4%.
Compound 5b from compound R8b: 38.1%.
Compound 5c from compound R8c: 66.8%.

EXAMPLE 6

4-amino-5-hydroxy-2-(4-methoxy)phenyl-2,3,4,5-tetrahydro-1-benzoxepin (Compounds 6a, 6b, and 6c)

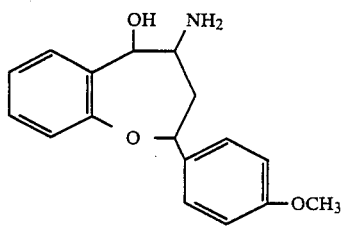

Compound 6a from compound R9a: 72.2%.
Compound 6b from compound R9b: 89.3%.
Compound 6c from compound R9c: 84.3%.

EXAMPLE 7

4-amino-5-hydroxy-2-(4-chloro)phenyl-2,3,4,5-tetrahydro-1-benzoxepin (Compounds 7a, 7b and 7c)

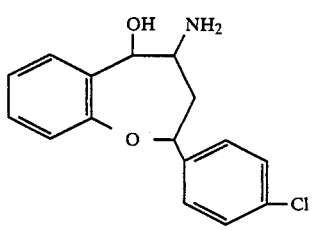

Compound 7a from compound R10a: 57.3%.
Compound 7b from compound R10b: 73.7%.
Compound 7c from compound R10c: 68.5%.

EXAMPLE 8

4-amino-5-hydroxy-2-(4-methyl)phenyl-2,3,4,5-tetrahydro-1-benzoxepin (Compounds 8a, 8b and 8c)

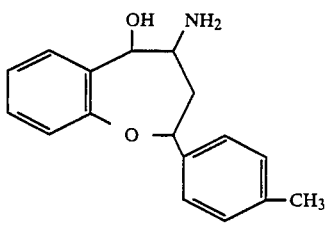

Compound 8a from compound R11a: 41.7%.
Compound 8b from compound R11b: 37.8%.
Compound 8c from compound R11c: 56.6%.

EXAMPLE 9

4-amino-5-hydroxy-2-(4-trifluoro)phenyl-2,3,4,5-tetrahydro-1-benzoxepin (Compounds 9a, 9b and 9c)

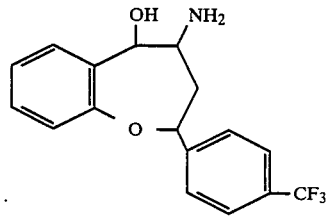

Compound 9a from compound R12a: 37.5%.
Compound 9b from compound R12b: 63.6%.
Compound 9c from compound R12c: 64.5%.

EXAMPLE 10

4-amino-5-hydroxy-2-(4-methoxycarbonyl)phenyl-2,3,4,5-tetrahydro-1-benzoxepin (Compounds 10a, 10b and 10c)

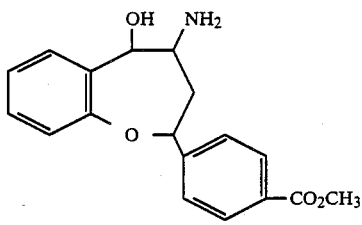

220 mg (0.42 m moles) of 4-acetamido-5-hydroxy-2-(4-methoxycarbonyl)phenyl-2,3,4,5-tetrahydro-1-benzoxepin (R13a, R13b or R13c; compounds of Reference Example 13) was dissolved in 7.5 ml of methanol, 7.5 ml of 10% sodium hydroxide aqueous solution was added to the resulting solution, and the whole was heated to reflux for 24 hours, and then cooled. Hydrochloric acid was added to the reaction mixture to acidify the mixture, which was concentrated to dryness under a reduced pressure by an aid of benzene. The residue was dissolved in methanol and then etheric solution of diazomethane were added, and the whole was stirred for an hour. After distilling off the solvent, the residue was partitioned between a mixture of methylene chloride/ethyl acetate (1:1) and a saturated aqueous solution of potassium carbonate. Phases were separated, and the aqueous phase was extracted with methylene chloride. The organic phases were combined and the combined organic phase was dried with anhydrous magnesium sulfate. The magnesium sulfate was then filtrated off, and the filtrate was concentrated to obtain a residue. The residue was separated by silica gel thin layer chromatography and a mixture of methylene chloride/methanol (9:1), to obtain stereoisomers 10a (14.5 mg; yield 23.1%), 10b (5 mg; yield 3.8%), and 10c (5 mg; yield 3.8%) of the compound of this invention.

EXAMPLE 11

4-amino-5,8-dihydroxy-2-phenyl-2,3,4,5-tetrahydro-1-benzoxepin (Compounds 11a, 11b, 11c and 11d)

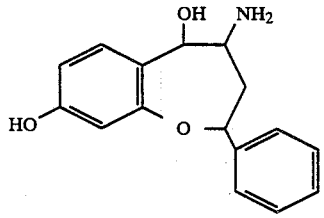

According to the same procedure as described in Example 1 (different process), 385 mg (1.36 m moles) of corresponding oxime, 2-phenyl-4-hydroxyimino-8-hydroxy-2,3,4,5-tetrahydro-1-benzoxepin-5-one was reduced to obtain stereoisomers 11a (30 mg), 11b (22 mg), 11c (21 mg), and 11d (9.6 mg) of the compound of this invention.

EXAMPLE 12

5-hydroxy-4-(4-methylpiperazinyl)-2-phenyl-2,3,4,5-tetrahydro-1-benzoxepin (Compounds 12a and 12b)

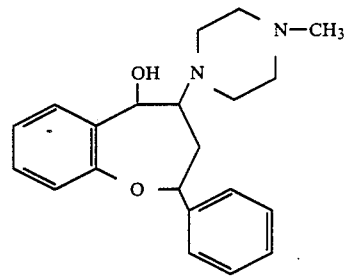

883 mg (2.13 m moles) of 4-(4-methylpiperazinyl)-2-phenyl-2,3,4,5-tetrahydro-1-benzoxepin-5-one (compound of Reference Example 15) was dissolved in 50 ml of methanol, 324 mg (4 molecular equivalent) of sodium borohydride was added to the solution under ice-cooling, and the whole was stirred for 3 hours. The reaction mixture was concentrated, and the residue was added to ice-water and then extracted with methylene chloride. The extract was washed with water and dried with anhydrous magnesium sulfate. After filtrating off the magnesium sulfate, the filtrate was concentrated to obtain a residue, which was then applied to a silica gel column and eluted with a mixture of methylene chloride/methanol (95:5) to obtain stereoisomers 12a (482 mg; yield 54.3%) and 12b (167 mg; yield 18.8%) of the compound of this invention.

EXAMPLE 13

5-hydroxy-4-methylamino-2-phenyl-2,3,4,5-tetrahydro-1-benzoxepin (Compounds 13a, 13b, 13c and 13d)

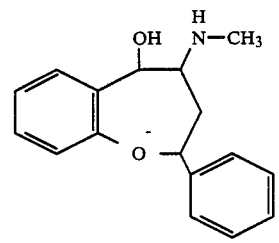

The same procedure as described in Example 12 was repeated except that 4-methylamino-2-phenyl-2,3,4,5-tetrahydro-1-benzoxepin-5-one (compound of Reference Example 16) was used as a starting compound to obtain two stereoisomers 13a (yield 23.6%) and 13b (yield 31.4%) of the compound of this invention.

Alternatively, the compounds of this invention were synthesized according to the following different process; wherein 286 mg (1.02 m moles) of 9-phenyl-9,10,10a, 3a-tetrahydro-[1]-benzoxepino-[4,5-d]oxazolidin-2-one (compound R25c of Reference Example 25) was dissolved in 500 ml of tetrahydrofuran, 155.2 mg (4.08 m moles) of lithium aluminium hydride was added to the solution under ice-cooling, and the whole was heated to reflux for 2 hours. A 3N sodium hydroxide aqueous solution was added to the reaction mixture to destroy excess lithium aluminium hydride, and a supernatant was separated, washed with water, and dried with anhydrous magnesium sulfate. After filtrating off the magnesium sulfate, the filtrate was concentrated, and the residue was applied to a silica gel column and eluted with a mixture of methylene chloride/methanol (97:3) to obtain 237 mg (yield 86.4%) of the compound 13c of this invention.

Moreover, the stereoisomer R25d of the Reference Example was treated according to the same procedure as described above, to obtain the compound 13d (yield 82.5%) of this invention.

EXAMPLE 14

5-hydroxy-4-dimethylamino-2-phenyl-2,3,4,5-tetrahydro-1-benzoxepin (Compounds 14a, 14b, 14c, and 14d)

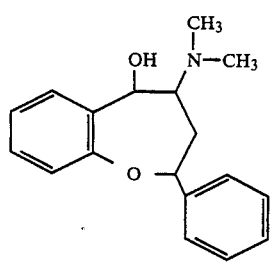

The same procedure as described in Example 12 was repeated except that 4-dimethylamino-2-phenyl-2,3,4,5-tetrahydro-1-benzoxepin-5-one (compoud of Reference Example 17) was used as a starting compound to obtain two stereoisomers 14a (yield 59.9%) and 14b (yield 18.9%) of the compound of this invention.

The compound of this invention was also synthesized according to the following different procedure. That is, each of compounds R27c and R27d of the Reference Example was reduced according to the same procedure as described in Example 13 (different process) to obtain stereoisomers 14c (yield 88.3%) and 14d (yield 84.1%) of the compound of this invention.

EXAMPLE 15

5-hydroxy-4-isopropylamino-2-phenyl-2,3,4,5-tetrahydro-1-benzoxepin (Compounds 15a and 15b)

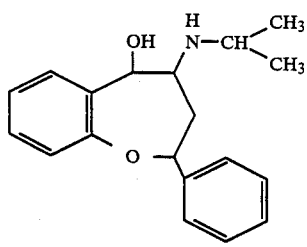

1.02 g (3.22 m moles) of 4-bromo-2-phenyl -2,3,4,5-tetrahydro-1-benzoxepin-5-one (compound R14 of the Reference Example) was dissolved in 60 ml of tetrahydrofuran, 5.71 g (30 mole equivalent) of isopropylamine was added to the solution, and the whole was stirred overnight. The reaction mixture was cooled, and under ice-cooling, 725 mg (19.1 m moles) of sodium borohydride and 10 ml of methanol were added to the reaction mixture, which was then stirred for 6 hours at a room temperature. The reaction mixture was concentrated, ice water was added to the concentrate, and the whole was extracted with methylene chloride. The resulting extract was washed with water and dried with anhydrous magnesium sulfate. After filtrating off the magnesium sulfate, the filtrate was concentrated to obtain a residue, which was then applied to a silica gel column, and eluted with a mixture of methylene chloride/methanol (98:2) to obtain stereoisomers 15a (255 mg; yield 26.7%) and 15b (120 mg; yield 12.6%) of the compound of this invention.

EXAMPLE 16

4-benzylamino-5-hydroxy-2-phenyl-2,3,4,5-tetrahydro-1-benzoxepin (Compounds 16b and 16c)

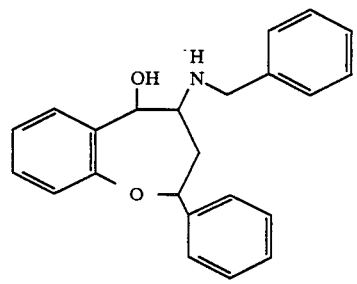

150 mg (0.56 m moles) of 4-amino-5-hydroxy-2-phenyl-2,3,4,5-tetrahydro-1-benzoxepin (compound 1b of Example 1) was dissolved in 25 ml of dioxane, and 813 mg (5.9 m moles) of potassium carbonate and 0.87 ml (0.17 m moles) of benzylbromide were added to the solution, which was then heated to reflux overnight. After distilling off the solvent, water was added to the residue, which was then extracted with methylene chloride, and the extract was dried with anhydrous magnesium sulfate. After filtrating off the magnesium sulfate, the filtrate was concentrated to obtain a residue, which was then applied to a silica gel column, and eluted with a mixture of methylene chloride/methanol (98:2) to obtain 56.9 mg (yield 42.0%) of the compound 16b of this invention.

The same procedure as described above was repeated except that stereoisomer 1c was used as a starting compound to obtain the compound 16c (yield 38.4%) of this invention.

EXAMPLE 17

5-hydroxy-4-phenethyl-2-phenyl-2,3,4,5-tetrahydro-1-benzoxepin (Compounds 17a, 17b, 17c and 17d)

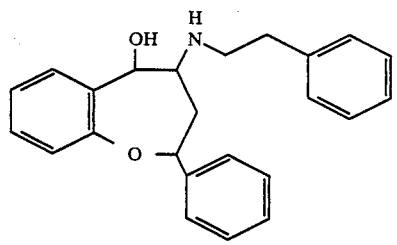

180 mg (0.71 m moles) of 4-amino-5-hydroxy-2-phenyl-2,3,4,5-tetrahydro-1-benzoxepin (compound 1a of Example 1) was dissolved in 36 ml of dioxane, and 0.58 ml (6 mole equivalent) of phenethyl bromide was added to the solution, which was then heated to reflux overnight. After distilling off the solvent, water was added to the residue, which was then extracted with methylene chloride, and the extract was dried with anhydrous magnesium sulfate. After filtrating off the magnesium sulfate, the filtrate was concentrated to obtain a residue, which were then applied to a silica gel column, and eluted with a mixture of methylene chloride/methanol (98:2) to obtain 96.8 mg (yield 38.2%) of the compound 17a of this invention.

The same procedure as described above was repeated except that each of stereoisomers 1b, 1c, and 1d was used as a starting compound to obtain the compounds 17b (yield 42.3%), 17c (yield 62.3%), and 17d (yield 87.7%), respectively, of this invention.

EXAMPLE 18

5-hydroxy-4-phenylpropylamino-2-phenyl-2,3,4,5-tetrahydro-1-benzoxepin (Compounds 18b and 18c)

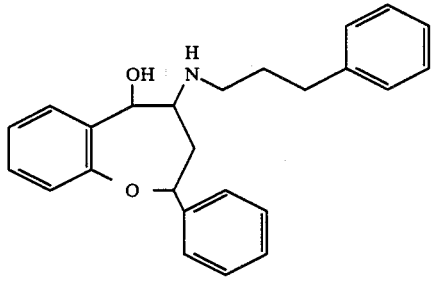

100 mg (0.392 m moles) of 4-amino-5-hydroxy-2-phenyl-2,3,4,5-tetrahydro-1-benzoxepin (compound 1b of Example 1) was dissolved in 20 ml of dioxane, and 271 mg (1.96 m moles) of potassium carbonate and 0.18 ml (1.18 m moles) of phenylpropyl bromide were added to the solution, which was then heated to reflux overnight. After distilling off the solvent, water was added to the residue, which was then extracted with methylene chloride. The extract was washed with water and dried with anhydrous magnesium sulfate. After filtrating off the magnesium sulfate, the filtrate was concentrated to obtain a residue, which was then applied to a silica gel column, and eluted with a mixture of methylene chloride/methanol (98:2) to obtain 100 mg (yield 68.5%) of the compound 18b of this invention.

The same procedure as described above was repeated except that stereoisomer 1c was used as a starting compound to obtain the corresponding compound 18c (yield 71.8%) of this invention.

EXAMPLE 19

5-hydroxy-4-(2-pyrid-3-ylethyl)amino-2-phenyl-2,3,4,5-tetrahydro-1-benzoxepin (Compound 19c)

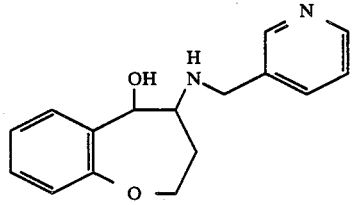

500 mg of 4-amino-5-hydroxy-2-phenyl-2,3,4,5-tetrahydro-1-benzoxepin (compound 1c of Example 1) was dissolved in 30 ml of dimethylformamide, and 2.76 ml (19.6 m moles) of triethylamine and 772 mg (4.7 moles) of 3-picolylchloride hydrochloride were added to the solution, which was then stirred at 45° C. for 18 hours. After distilling off dimethylformamide, sodium bicarbonate aqueous solution was added to the residue, which was then extracted with methylene chloride. The extract was washed with water and dried with anhydrous magnesium sulfate. After filtrating off the magnesium sulfate, the filtrate was concentrated to obtain a residue, which was then applied to a silica gel column, and eluted with a mixture of methylene chloride/methanol (97:3) to obtain 305 mg (yield 45.0%) of the compound 19c of this invention.

EXAMPLE 20

5-hydroxy-4-4-[2-(4-methoxyphenyl)ethyl]amino-2-(4-methoxyphenyl)-2,3,4,5-tetrahydro-1-benzoxepin (Compound 20c)

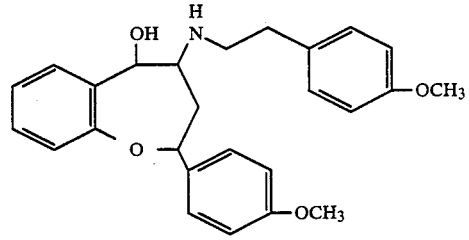

According to the same procedure as described in Example 19, 4-amino-5-hydroxy-2-(4-methoxyphenyl)-2,3,4,5-tetrahydro-1-benzoxepin (compound 6c of Example 6) was reacted with 4-methoxyphenylethyl bromide in the presence of triethyl amine to obtain the compound 20c (yield 40.8%) of this invention.

EXAMPLE 21

5-hydroxy-4-(3-phenylpropyl)amino-2-(4-methoxyphenyl)-2,3,4,5-tetrahydro-1-benzoxepin (Compound 21c)

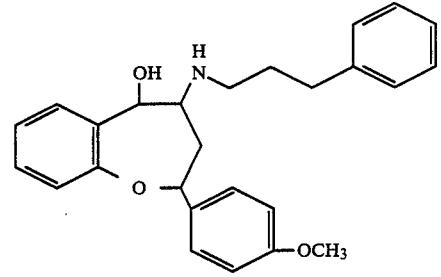

According to the same procedure as described in Example 19, 4-amino-5-hydroxy-2-(4-methoxyphenyl)-2,3,4,5-tetrahydro-1-benzoxepin (compound 6c of Example 6) was reacted with phenylpropyl bromide in the presence of triethyl amine to obtain the compound 21c (yield 33.9%) of this invention.

EXAMPLE 22

8-chloro-5-hydroxy-4-(2-phenylethyl)amino-2-phenyl-2,3,4,5-tetrahydro-1-benzoxepin (Compound 22a)

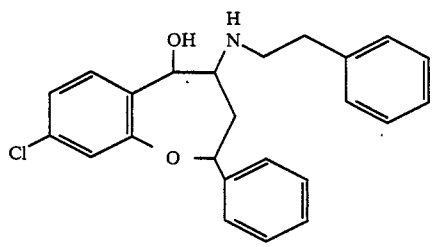

According to the same procedure as described in Example 17, 4-amino-5-hydroxy-8-chloro-2-phenyl-2,3,4,5-tetrahydro-1-benzoxepin (compound 4a of Example 4) was used as a starting compound to obtain the compound 22a (yield 88%) of this invention.

EXAMPLE 23

8-chloro-5-hydroxy-4-(3-phenylpropyl)amino-2-phenyl-2,3,4,5-tetrahydro-1-benzoxepin (Compound 23a)

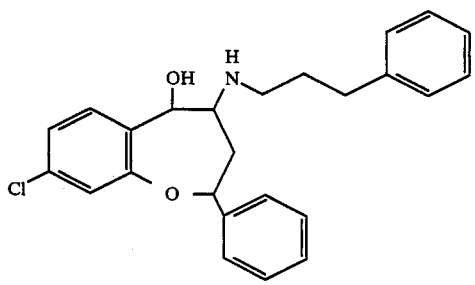

According to the same procedure as described in Example 17, 4-amino-5-hydroxy-8-chloro-2-phenyl-2,3,4,5-tetrahydro-1-benzoxepin (compound 4a of Example 4) was used to obtain the compound 23a (yield 81%) of this invention.

EXAMPLE 24

5-hydroxy-4-(2-phenylethyl)amino-2-(4-methoxycarbonylphenyl)-2,3,4,5-tetrahydro-1-benzoxepin (Compound 24b)

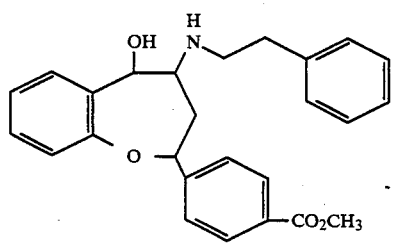

According to the same procedure as described in Example 17, 4-amino-5-hydroxy-2-(4-methoxycarbonylphenyl)-2,3,4,5-tetrahydro-1-benzoxepin (compound 10b of Example 10) was used as a starting compound to obtain the compound 24b (yield 51%) of this invention.

EXAMPLE 25

5-hydroxy-4-(4-phenylbutyl)amino-2-phenyl-2,3,4,5-tetrahydro-1-benzoxepin (Compounds 25b and 25c)

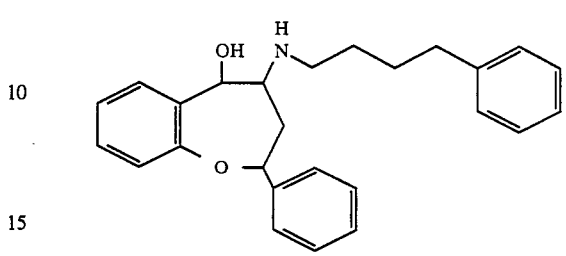

278 mg (0.72 m moles) of 5-hydroxy-4-(1-oxo-4-phenylbutyl)amino-2-phenyl--2,3,4,5-tetrahydro-1-benzoxepin (compound R19b of Refference Example 19) was dissolved in 50 ml of tetrahydrofuran, and 220 mg (5.8 m moles) of lithium aluminium hydride was added to the solution, which was then heated to reflux for 17 hours. A 3N sodium hydroxide aqueous solution was added to the reaction mixture under ice-cooling, a supernatant was separated, and the supernatant was dried with anhydrous magnesium sulfate. After filtrating off the magnesium sulfate, the filtrate was concentrated to obtain a residue, which was then applied to a silica gel column and eluted with a mixture of methylene chloride/methanol (98:2) to obtain 175 mg (yield 65.3%) of the compound 25b of this invention.

Stereoisomer R19c of Reference Example 19 was treated according to the same procedure as described above to obtain the compound 25c (yield 75.7%) of this invention.

The same procedure as described in Example 25 was repeated except that compounds of Reference Examples 20, 21, 22, 23, and 24 were used as starting compounds to obtain compounds 26 to 30.

EXAMPLE 26

5-hydroxy-4-[2-(p-methoxyphenyl)ethyl]amino-2-phenyl-2,3,4,5-tetrahydro-1-benzoxepin (Compounds 26a, 26b, and 26c)

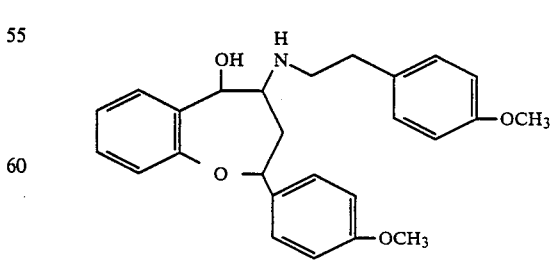

Compound 26a from compound R20a: 92%.
Compound 26b from compound R20b: 71%.
Compound 26c from compound R20c: 87%.

EXAMPLE 27

5-hydroxy-4-[2-(4-hydroxyphenyl)ethyl]amino-2-phenyl-2,3,4,5-tetrahydro-1-benzoxepin (Compounds 27a, 27b, and 27c)

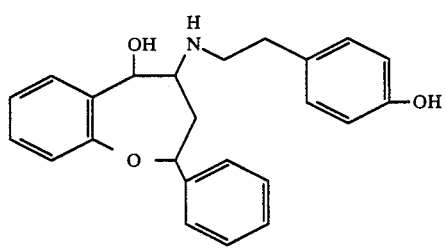

Compound 27a from compound R21a: 85%.
Compound 27b from compound R21b: 80%.
Compound 27c from compound R21c: 92%.

EXAMPLE 28

5-hydroxy-4-[2-(3,4-dimethoxyphenyl)ethyl]amino-2-phenyl-2,3,4,5-tetrahydro-1-benzoxepin (Compounds 28b and 28c)

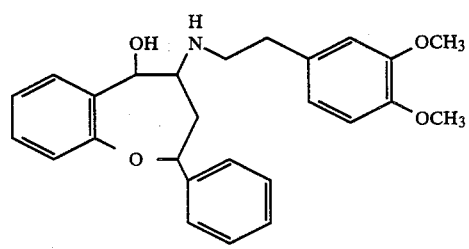

Compound 28b from compound R22b: 78%.
Compound 28c from compound R22c: 82%.

EXAMPLE 29

5-hydroxy-4-[2-(3,4-dihydroxyphenyl)-ethyl]amino-2-phenyl-2,3,4,5-tetrahydro-1-benzoxepin (Compounds 29a, 29b, and 29c)

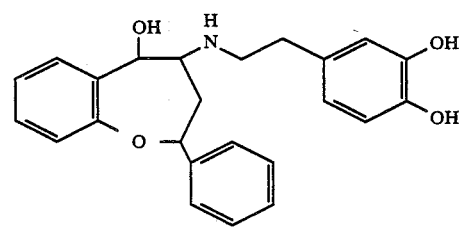

Compound 29a from compound R23a: 36%.
Compound 29b from compound R23b: 66%.
Compound 29c from compound R23c: 64%.

EXAMPLE 30

5-hydroxy-4-(2-pyrid-3-ylethyl)amino-2-phenyl-2,3,4,5-tetrahydro-1-benzoxepin (Compounds 30b and 30c)

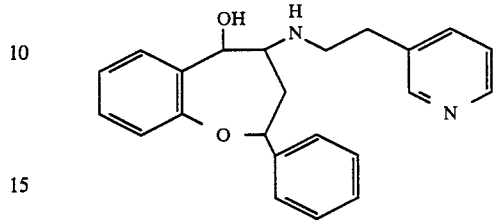

Compound 30b from compound R24b: 32%.
Compound 30c from compound R24c: 28%.

EXAMPLE 31

5-hydroxy-4-(N-methyl-N-phenylethyl)amino-2-phenyl-2,3,4,5-tetrahydro-1-benzoxepin (Compounds 31b and 31c)

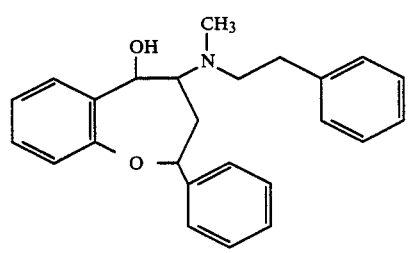

261 mg (0.68 m moles) of 1-phenylethyl-9,10,10a,3a-tetrahydro-[1]-benzoxepino[4,5-d]oxazolidin-2-one (compound R26b of Reference Example 26 was dissolved in 60 ml of tetrahydrofuran, and 103 mg (2.71 m moles) of lithium aluminium hydride was added to the solution, which was then heated to reflux for 6 hours. 3N sodium hydroxide aqueous solution was added to the reaction mixture under ice-cooling to destroy excess lithium aluminium hydride, and a supernatant was separated. The supernatant was dried with anhydrous magnesium sulfate. After filtrating off the magnesium sulfate, the filtrate was concentrated to obtain a residue, which was then applied to a silica gel column, and eluted with a mixture of hexane/ethyl acetate (85:15) to obtain 162 mg (yield 64.1%) of the compound 31b of this invention.

Stereoisomer R26c of Reference Example 26 was treated according to the same procedure as described above to obtain the corresponding compound 31c (yield 69.9%) of this invention.

EXAMPLE 32

5-hydroxy-4-(N-methyl-N-(3-phenyl)propyl)amino-2-phenyl-2,3,4,5-tetrahydro-1-benzoxepin (Compounds 32b and 32c)

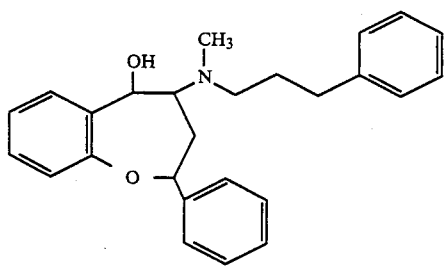

Each of compounds R28b and R28c of Reference Example 28 was treated according to the same procedure as described in Example 31 to obtain the compounds 32b (yield 85.0%) and 32c (yield 59.4%) of this invention.

EXAMPLE 33

5-hydroxy-4-(2-pyridin-2-yl)ethylamino-2-phenyl-2,3,4,5-tetrahydro-1-benzoxepin (Compound 33c)

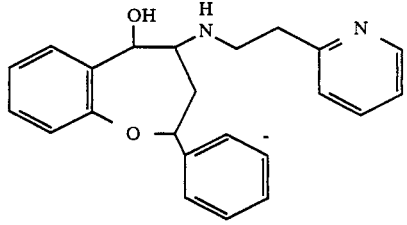

380 mg of 1-(2-pyridin-2-yl)ethyl-9-phenyl-9,10,10a,-3a-tetrahydro-[1]-benzoxepino[4,5-d]oxazolidin-2-one (compound R29c of Reference Example) was dissolved in 50 ml of ethanol, and 50 ml of 4N sodium hydroxide aqueous solution was added to the solution, which was then heated to reflux for 2 hours. After cooling, water was added to the reaction mixture, which was then extracted with methylene chloride. The extract was washed with water and dried with anhydrous magnesium sulfate. After filtrating off the magnesium sulfate, the filtrate was concentrated to obtain the 210 mg (yield 59.3%) of the compound 33c of this invention.

TABLE 1

Structure:

Core: 2-phenyl-chroman-type with OH and NR³R⁴ substituents; R¹ and R² on fused benzene (positions 6,7,8,9); R⁵ on phenyl ring.

| Exp. No. (Comp. No.) | R¹ | R² | R³ | R⁴ | R⁵ | Melting Point (°C.) (Appearance) | IR Spectrum | NMR Spectrum |
|---|---|---|---|---|---|---|---|---|
| 1 (1a) | H | H | H | H | H | 129–131 | 3200, 3050, 2920 1600, 1580, 1480 1460, 1350, 1260 1220, 1050, 960 760, 695 | 2.08(m, 1H, H-3α)2.43(m, 1H, H-3β) 2.40(br, s, 3H, OH, NH₂)3.47(m, 1H, H-4) 4.83(dd, 1H, J=11, 2Hz, J=2.0Hz, H-5) 5.17(s, 1H, H-2) 6.98–7.50(m, 8H, arom) |
| 1 (1b) | H | H | H | H | H | (oil) | 3350, 3060, 2900 1600, 1580, 1490 1460, 1220, 1050 980, 760, 700 | 7.51(d, 1H, J=7.2Hz, H-6) 1.90(m, 1H, H-3α)2.55(m, 1H, H-3β) 2.57 (br, s, 3H, OH, NH₂) 3.44(m, 1H, H-4) 4.77(d, 1H, J=7.2Hz, H-5) 5.13(dd, 1H, J=11.9Hz, J=2.0Hz, H-2) 6.98–7.50(m, 9H, arom) |
| 1 (1c) | H | H | H | H | H | 196.5–198 | 3350, 3300, 3100 1600, 1570, 1480 1440, 1350, 1260 1225, 1060, 980 880, 760, 695 | 2.28–2.45(m, 2H, H-3)3.00(m, 1H, H-4) 4.25(br, s, 3H, OH, NH₂) 4.50(d, 1H, J=10.6Hz, H-5) 4.86(d, 1H, J=9.9Hz, H-2) 7.66(d, 1H, J=6.26Hz, H-6) 6.91–7.46(m, 8H, arom) |
| 1 (1d) | H | H | H | H | H | 186–188 | 3400, 3320, 2900 1600, 1580, 1480 1450, 1350, 1230 1050, 990, 910 755, 690 | 2.10(br, s, 3H, OH, NH₂)2.17(m, 1H, H-3α)2.45(m, 1H, H-3β)3.38(m, 1H, H-4) 4.74(s, 1H, H-5) 4.84(d, 1H, H=11.9Hz, H-2) 7.00–7.45(m, 9H, arom) |
| 2 (2a) | —OCH₃ (7) | H | H | H | H | 159.5–160.5 | 3340, 3270, 3000 2900, 2805, 1600 1570, 1485, 1260 1205, 1095, 1040 980, 945, 880 800, 760, 700 | 1.99(br, s, 3H, OH, NH₂) 2.07(m, 1H, H-3α)2.43(m, 1H, H-3β) 3.46(s, 1H, H-4)3.80(s, 3H, OCH₃) 4.74(dd, 1H, J=1.3Hz, J=11.2Hz, H-2 or 5) 5.20(s, 1H, H-2 or 5) 6.69–7.44(m, 8H, arom) |
| 2 (2b) | —OCH₃ (7) | H | H | H | H | 104.0–105.0 | 3300, 2900, 2850 1605, 1590, 1500 1460, 1435, 1275 1200, 1150, 1040 985, 940, 700 | 1.96(m, 1H, H-3α) 2.38(br, s, 3H, OH, NH₂) 2.64(m, 1H, H-3β)3.49(m 1H, H-4) 3.78(s, 3H, OCH₃) 4.74(d, 1H, J=6.6Hz, H-2.25) 5.07(dd, 1H, J=2.0Hz, J=11.3Hz, H-2 or 5) 6.71–7.42(m, 8H, arom) |
| 2 | —OCH₃ | H | H | H | H | 154.5–155.5 | 3200, 2900, 1600 | 2.34(m, 1H, H-3α)2.94(m, 1H, H-4) |

TABLE 1-continued

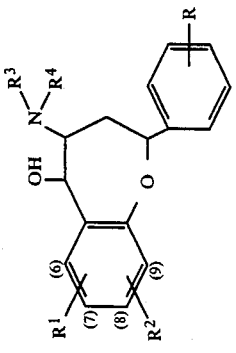

| Exp. No. (Comp. No.) | Substituent R¹ | R² | R³ | R⁴ | R⁵ | Melting Point (°C.) (Appearance) | IR Spectrum | NMR Spectrum |
|---|---|---|---|---|---|---|---|---|
| (2c) | (7) | | | | | | 1580, 1485, 1260 1200, 1140, 1055 1030, 755, 690 | 3.60(br, s, 3H, OH, NH₂) 3.75(s, 3H, OCH₃) 4.51(d, 1H, J=10.6Hz, H-2 or 5) 4.78(d, 1H, J=9.9Hz, H-2 or 5) 6.65–7.39(m, 8H, arom) |
| 3 (3a) | H | —OCH₃ (8) | H | H | H | 157–159 | 3320, 2900, 1605 1570, 1490, 1440 1190, 1150, 1030 900, 750, 695 | 2.05–2.13(m, 1H, H-3α) 2.37–2.48(m, 1H, H-3β) 2.55(br, s, 3H, OH, NH₂) 3.46–3.50(m, 1H, H-4)3.73(s, 3H, OMe) 4.09(dd, 1H, J=2.0Hz, J=11.2Hz, H-5) 5.07(s, 1H, H-2) 6.56(d, 1H, J=2.0Hz, H-9) 6.66(dd, 1H, J=2.0Hz, J=8.6Hz, H-7) 7.27–7.43(m, 6H, arom) |
| 3 (3b) | H | —OCH₃ (8) | H | H | H | 92–94 | 3350, 3050, 2900 1610, 1495, 1440 1270, 1190, 1160 1120, 1030, 905 730, 695 | 1.87–1.95(m, 1H, H-3α) 2.59(br, s, 3H, NH₂, OH) 2.62–2.73(m, 1H, H-3β) 3.39–3.45(m, 1H, H-4) 3.72(s, 3H, OMe) 4.68(d, 1H, J=6.6Hz, H-5) 5.07(d, 1H, J=9.9Hz, H-2) 6.55(d, 1H, J=2.6Hz, H-9) 6.60(dd, 1H, J=2.6Hz, J=8.6Hz, H-7) 7.24–7.42(m, 6H, arom) |
| 3 (3c) | H | —OCH₃ (8) | H | H | H | 137–139 | 3350, 3050, 2900 1610, 1575, 1490 1440, 1190, 1155 1120, 1060, 1030 910, 730, 695 | 1.55(br, s, 3H, OH, NH₂) 2.13–2.27(m, 1H, H-3α) 2.32–2.40(m, 1H, H-3β) 2.75–2.84(m, 1H, H-4)3.76(s, 3H, OMe) 4.59(d, 1H, J=10.5Hz, H-5) 4.64(d, 1H, J=10.5Hz, H-2) 6.58(d, 1H, J=2.6Hz, H-9) 6.74(dd, 1H, J=2.6Hz, J=8.6Hz, H-7) 7.22–7.47(m, 5H, arom) |
| 4 (4a) | H | Cl (8) | H | H | H | 126–128 | 3350, 3050, 2900 1595, 1570, 1480 1400, 1220, 1020 | 2.12(m, 1H, H-3α)2.44(m, 1H, H-3β) 2.95(br, s, 3H, OH, NH₂)3.52(m, 1H, H-4) 4.88(dd, 1H, J=2.0Hz, J=11.2Hz, H-2) 7.64(d, 1H, J=8.6Hz, H-6) |

TABLE 1-continued

Structure:

OH, NR³R⁴ groups on a chromane-type bicyclic system with phenyl bearing R substituent; positions 6, 7, 8, 9 on benzo ring with R¹ (7), R² (8), R⁵.

| Exp. No. (Comp. No.) | R¹ | R² | R³ | R⁴ | R⁵ | Melting Point (°C.) (Appearance) | IR Spectrum | NMR Spectrum |
|---|---|---|---|---|---|---|---|---|
| 4 (4b) | H | Cl (8) | H | H | H | 74–76 | 960, 905, 730 695 | 5.11(d, 1H, J=2.0Hz, H-5) 7.02(d, 1H, J=2.6Hz, H-9) 7.08(dd, 1H, J=2.6Hz, J=8.6Hz, H-7) 7.27–7.52(m, 6H, arom) |
| 4 (4c) | H | Cl (8) | H | H | H | 153–155 | 3350, 3050, 2900 1595, 1570, 1480 1405, 1220, 1120 1080, 1030, 980 940, 815, 730 695 | 1.95(m, 1H, H-3α)2.62(m, 1H, H-3β) 2.98(br, s, 3H, OH, NH₂)3.43(m, 1H, H-4) 4.82(d, 1H, J=7.9Hz, H-5) 5.19(dd, 1H, J=2.0Hz, J=11.2Hz, H-2) 6.99(d, 1H, J=2.0Hz, H-9) 7.04(dd, 1H, J=2.0Hz, J=8.6Hz, H-7) 7.28–7.52(m, 6H, arom) |
| 4 (4d) | H | Cl (8) | H | H | H | 156–158 | | 2.26(m, 1H, H-3α)2.38(m, 1H, H-3β) 2.81(br, s, 3H, OH, NH₂) 4.58(dd, 1H, J=2.0Hz, J=11.2Hz, H-2) 4.65(d, 1H, J=9.2Hz, H-5) 7.02(d, 1H, J=2.0Hz, H-9) 7.13(dd, 1H, J=2.0Hz, J=8.6Hz, H-7) 7.27–7.45(m, 5H, arom) 7.17(d, 1H, J=8.6Hz, H-6) 2.08(m, 1H, H-3α) 2.22(br, s, 3H, OH, NH₂) 2.28(m, 1H, H-3β)3.29(m, 1H, H-4) 4.70(d, 1H, J=2.0Hz, H-5) 4.85(d, 1H, J=11.2Hz, H-2) 7.01(d, 1H, J=2.0Hz, H-5) 7.05(d, 1H, J=2.0Hz, J=7.9Hz, H-7) 7.10–7.49(m, 6H, arom) |
| 5 (5a) | —OCH₃ (7) | —OCH₃ (8) | H | H | H | (Powder) | 3300, 2930, 2830 1605, 1505, 1445 1400, 1350, 1260 1210, 1195, 1120 1030, 1005, 905 875, 725, 695 | 2.16(m, 1H, H-3α)2.48(m, 1H, H-3β) 2.64(br, s, 3H, OH, NH₂) 3.56(m, 1H, H-4)3.86(s, 3H, OCH₃) 3.86(s, 3H, OCH₃)3.93(s, 3H, OCH₃) 4.89(d, 1H, J=11.9Hz, H-2 or 5) 5.20(s, 1H, H-2 or 5)² 6.05(s, 1H, H-9)7.15(s, 1H, H-6) 7.34–7.55(m, 5H, arom) |
| 5 (5b) | —OCH₃ (7) | —OCH₃ (8) | H | H | H | 110–112 | 3250, 1600, 1500 1440, 1400, 1205 | 1.61(br, s, 3H, OH, NH₂) 1.95(m, 1H, H-3α), 2.75(m, 1H, H-3β) |

TABLE 1-continued

[Structure: chromene-type with OH, N(R³)(R⁴), phenyl with R substituent, and R¹ at position 7, R² at position 8, positions 6 and 9 on benzene ring]

| Exp. No. (Comp. No.) | Substituent R¹ | R² | R³ | R⁴ | R⁵ | Melting Point (°C.) (Appearance) | IR Spectrum | NMR Spectrum |
|---|---|---|---|---|---|---|---|---|
| 5 (5c) | —OCH₃ (7) | —OCH₃ (8) | H | H | H | 160–161 | 1190, 1165, 1115 1060, 100, 755 690 | 3.48(m, 1H, H-4), 3.81(s, 3H, OCH₃) 3.89(s, 3H, OCH₃) 4.62(d, 1H, J=6.6Hz, H-2 or 5) 5.02(dd, 1H, J=2.0Hz, J=11.9Hz, H-2 or 5) 6.59(s, 1H, H-9)6.89(s, 1H, H-6) 7.29–7.46(m, 5H, arom) |
| 6 (6a) | H | H | H | H | —OCH₃ (p) | 128.0–129.0 | 3350, 3300, 3100 2900, 2820, 1605 1570, 1500, 1460 1440, 1260, 1210 1190, 1125, 1005 875, 760, 750 700 | 2.14–2.36(m, 2H, H-3)2.85(m, 1H, H-4) 3.04(br, s, 3H, OH, NH₂) 3.80(s, 3H, OCH₃)3.90(s, 3H, OCH₃) 4.59(d, 1H, J=10.6Hz, H-2 or 5) 4.67(d, 1H, J=10.6Hz, H-2 or 5) 6.58(s, 1H, H-9) 7.39–7.48(m, 6H, arom) |
| 6 (6b) | H | H | H | H | —OCH₃ (p) | 123.0–124.0 | 3340, 3270, 3050 2900, 1600, 1580 1505, 1480, 1450 1345, 1235, 1175 1040, 1030, 950 820, 800, 760 | 1.90(br, s, 3H, OH, NH₂) 2.07(m, 1H, H-3α)2.50(m, 1H, H-3β) 3.50(m, 1H, H-4)3.83(s, 3H, OCH₃) 4.81(dd, 1H, J=2.0Hz, J=11.2Hz, H-2 or 5) 5.18(d, 1H, J=2.0Hz, H-2 or 5) 6.90–7.40(m, 7H, arom) 7.54(m, 1H, H-6) |
| 6 (6c) | H | H | H | H | —OCH₃ (p) | 175.5–177.0 | 3150, 2900, 2830 1610, 1595, 1580 1510, 1480, 1450 1300, 1255, 1225 1175, 1050, 1030 980, 895, 810 770, 750 | 1.97(m, 1H, H-3α)2.66(m, 1H, H-3β) 3.09(br, s, 3H, OH, NH₂) 3.49(m, 1H, H-4)3.79(s, 3H, OCH₃) 5.12(dd, 1H, J=7.3Hz, J=11.9Hz, H-2 or 5) 6.85–7.42(m, 8H, arom) |
| 7 (7a) | H | H | H | H | Cl (p) | 152.0–153.0 | 3330, 3270, 2900 1605, 1580, 1505 1475, 1240, 1220 1175, 1060, 1030 940, 855, 805 755 | 2.23–2.40(m, 2H, H-3), 2.92(m, 1H, H-4) 3.32(br, s, 3H, OH, NH₂) 3.81(s, 3H, OCH₃) 4.54(dd, 1H, J=2.6Hz, J=10.5Hz, H-2 or 5) 4.77(d, 1H, J=9.8Hz, H-2 or 5) 6.88–7.35(m, 7H, arom) 7.71(m, 1H, H-6) |
| | H | H | H | H | | | 3370, 3300, 3250 1600, 1570, 1470 1440, 1355, 1260 | 1.75(br, s, 3H, OH, NH₂) 2.07(m, 1H, H-3α)2.42(m, 1H, H-3β) 3.49(m, 1H, H-4) |

TABLE 1-continued

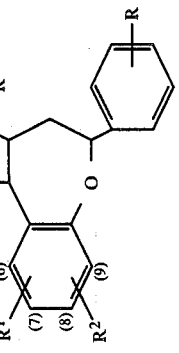

| Exp. No. (Comp. No.) | Substituent R¹ | R² | R³ | R⁴ | R⁵ | Melting Point (°C.) (Appearance) | IR Spectrum | NMR Spectrum |
|---|---|---|---|---|---|---|---|---|
| 7 (7b) | H | H | H | H | Cl (p) | 86.0–87.5 | 3230, 3050, 2850 1595, 1570, 1480 1440, 1250, 1230 1045, 1020, 980 900, 800, 750 | 1.95(m, 1H, H-3α), 2.59(m, 1H, H-3β) 3.07(br, s, 3H, OH, NH₂) 3.49(m, 1H, H-4) 4.85(d, 1H, J=7.9Hz, H-2 or 5) 5.14(d, 1H, J=2.0Hz, J=11.9Hz, H-2 or 5)6.94–7.41(m, 8H, arom) |
| 7 (7c) | H | H | H | H | Cl (p) | 171.0–172.0 | 3100, 2900, 2830 1600, 1580, 1480 1260, 1225, 1075 1010, 945, 760 | 2.22(m, 1H, H-3α)2.37(m, 1H, H-3β) 2.92(m, 1H, H-4) 3.12(br, s, 3H, OH, NH₂) 4.56(dd, 1H, J=2.0Hz, J=11.2Hz, H-2 or 5) 4.75(d, 1H, J=9.9Hz, H-2 or 5) 6.96–7.39(m, 7H, arom) 7.72(m, 1H, H-6) |
| 8 (8a) | H | H | H | H | —CH₃ (p) | 130–131 | 3320, 3050, 2900 1595, 1575, 1475 1445, 1340, 1260 1220, 1050, 1015 940, 900, 795 | 1.55(br, s, 3H, OH, NH₂) 2.07(m, 1H, H-3α), 2.37(s, 3H, CH₃) 2.48(m, 1H, H-3β), 3.48(m, 1H, H-4) 4.81(dd, 1H, J=4.7Hz, J=11.2Hz, H-2 or 5) 5.19(d, 1H, J=2.0Hz, H-2 or 5) 6.99–7.35(m, 7H, arom), 7.55(m, 1H, H-6) |
| 8 (8b) | H | H | H | H | —CH₃ (p) | 115–116 | 3100, 2900, 1600 1575, 1480, 1450 1250, 1225, 1055 1040, 1020, 900 800, 755 | 1.96(m, 1H, H-3α)2.34(s, 3H, CH₃) 2.64(m, 1H, H-3β) 3.20(br, s, 3H, OH, NH₂) 3.48(m, 1H, H-4) 4.84(d, 1H, J=7.9Hz, H-2 or 5) 5.12(d, 1H, J=2.0Hz, J=11.9Hz, H-2 or 5)6.94–7.34(m, 7H, arom) 7.41(m, 1H, H-6) |
| 8 (8c) | H | H | H | H | —CH₃ (p) | 169.5–170.5 | 3320, 3100, 2880 1595, 1575, 1475 1255, 1220, 1060 1030, 940, 810 750 | 2.20–2.40(m, 2H, H-3)2.36(s, 3H, CH₃) 2.90(m, 1H, H-4) 3.35(br, s, 3H, OH, NH₂) 4.55(dd, 1H, J=2.0Hz, J=10.5Hz, H-2 or 5) 4.75(d, 1H, J=9.9Hz, H-2 or 5) 6.96–7.32(m, 7H, arom) |

TABLE 1-continued

| Exp. No. (Comp. No.) | Substituent | | | | | Melting Point (°C.) (Appearance) | IR Spectrum | NMR Spectrum |
|---|---|---|---|---|---|---|---|---|
| | $R^1$ | $R^2$ | $R^3$ | $R^4$ | $R^5$ | | | |
| 9 (9a) | H | H | H | H | —CF$_3$ (p) | 156–157 | 3100, 2900, 2850 2750, 1620, 1585 1485, 1330, 1235 1165, 1120, 1070 1015, 860, 830 765, 690, 660 | 7.73(m, 1H, H-6) 1.60(br, s, 3H, OH, NH$_2$) 2.08(m, 1H, H-3α)2.41(m, 1H, H-3β) 3.50(m, 1H, H-4) 4.92(d, 1H, J=10.6Hz, H-2 or 5) 5.18(d, 1H, J=1.3Hz, H-2 or 5) 6.99–7.67(m, 8H, arom) |
| 9 (9b) | H | H | H | H | —CF$_3$ (p) | 116.0–116.5 | 3100, 2930, 2870 1615, 1600, 1575 1485, 1450, 1410 1320, 1235, 1160 1105, 1050, 820 755 | 1.77(br, s, 3H, OH, NH$_2$) 1.93(m, 1H, H-3α)2.70(m, 1H, H-3β) 3.51(m, H, H-4) 4.74(d, 1H, J=7.3Hz, H-2 or 5) 5.17(d, 1H, J=11.9Hz, H-2 or 5) 7.01–7.71(m, 8H, arom) |
| 9 (9c) | H | H | H | H | —CF$_3$ (p) | 162.5–164.0 | 3400, 3330, 3100 2850, 1620, 1600 1575, 1480, 1325 1220, 1160, 1135 1060, 830, 755 | 1.59(br, s, 3H, OHNH$_2$) 2.16(m, 1H, H-3α)2.38(m, 1H, H-3β) 2.85(m, 1H, H-4) 4.67(d, 1H, J=9.9Hz, H-2 or 5) 6.96–7.67(m, 7H, arom) 7.77(m, 1H, arom) |
| 10 (10a) | H | H | H | H | —CO$_2$CH$_3$ (p) | (white amorphous) | 3400–2800, 1730 1290, 1220, 1100 1050, 760 | 2.05(b, s, 3H, NH$_2$, OH) 2.06(m, 1H, H-3α)2.41(m, 1H, H-3β) 3.52(m, 1H, H-4)3.93(s, 3H, CO$_2$CH$_3$) 4.91(dd, 1H, J=11.2Hz, 2.0Hz, H-2) 5.18(s, 1H, H-5) 7.01(dd, 1H, J=7.9Hz, 2.0Hz, H-9) 7.19(m, 2H, H-7, H-8) 7.51(d, 2H, J=8.6Hz, H-2') 7.54(m, 1H, H-6) 8.05(d, 2H, J=8.6Hz, H-3') |
| 10 (10b) | H | H | H | H | —CO$_2$CH$_3$ | (white amorphous) | 3400–2800, 1720 1280, 1220, 1100 1060, 760 | 1.94(b, 4H, OH, NH$_2$, H-3α) 2.65(m, 1H, H-3β)3.49(m, 1H, H-4) 3.93(s, 3H, CO$_2$CH$_3$) 4.75(d, 1H, J=7.3Hz, H-5) 5.17(dd, 1H, J=11.9Hz, 1.3Hz, H-2) 7.03(dd, 1H, J=7.9Hz, 1.3Hz, H-9) 7.11(ddd, 1H, J=7.9Hz, 7.9Hz, 1.3Hz, H-7)7.26(ddd, 1H, J=7.9Hz, 7.9Hz, |

TABLE 1-continued

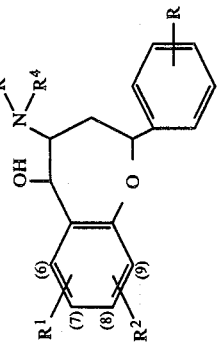

| Exp. No. (Comp. No.) | Substituent | | | | | Melting Point (°C.) (Appearance) | IR Spectrum | NMR Spectrum |
|---|---|---|---|---|---|---|---|---|
| | $R^1$ | $R^2$ | $R^3$ | $R^4$ | $R^5$ | | | |
| 10 (10c) | H | H | H | H | —$CO_2CH_3$ (p) | (white amorphous) | 3300-3000, 1720 1280, 1220, 1100 1050, 760 | 1.9Hz, H-8) 7.41(dd, 1H, J=7.9Hz, 1.9Hz, H-6) 7.51(d, 2H, J=7.9Hz, H-2') 8.06(d, 2H, J=7.9Hz, H-3') 2.25(m, 5H, OH, $NH_2$, H-3α, H-3β) 2.87(m, 1H, H-4) 3.93(s, 3H, $CO_2CH_3$) 4.67(m, 2H, H-5, H-2) 6.98(dd, 1H, J=5.3Hz, 1.3Hz, H-9) 7.20(m, 2H, H-7, H-8) 7.51(d, 2H, J=8.6Hz, H-2') 7.77(m, 1H, H-6) 8.05(d, 2H, J=8.6Hz, H-3') |
| 11 (11a) | H | OH (8) | H | H | H | (oil) | 3250, 3050, 2900 1620, 1590, 1500 1450, 1340, 1295 1230, 1150, 1100 1080, 1030, 975 730, 695 | 2.20(m, 1H, H-3α)2.43(m, 1H, H-3β) 3.05(m, 1H, H-4) 4.63(d, 1H, J=8.6Hz, H-5) 4.69(dd, 1H, J=10.9Hz, J=1.3Hz, H-2) 6.49(d, 1H, J=2.6Hz, H-9) 6.62(dd, 1H, J=8.6Hz, J=2.6Hz, H-7) 7.30-7.43(m, 5H, arom) 7.50(d, 1H, J=8.6Hz, H-6) |
| 11 (11b) | H | OH (8) | H | H | H | 164-166 | | 1.85(m, 1H, H-3α)2.09(m, 1H, H-3β) 3.53(m, 1H, H-4) 5.15(d, 1H, J=5.3Hz, H-5) 5.30(d, 1H, J=7.3Hz, H-2) 6.55(d, 1H, J=2.0Hz, H-9) 6.67(dd, 1H, J=2.0Hz, J=7.5Hz, H-7) 7.20-7.50(m, 5H, arom) 7.55(d, 1H, J=7.5Hz, H-6) |
| 11 (11c) | H | OH (8) | H | H | H | (oil) | | 2.28(m, 1H, H-3α)2.72(m, 1H, H-3β) 3.63(m, 1H, H-4) 5.00(d, 1H, J=9.9Hz, H-5) 5.30(dd, 1H, J=11.9Hz, J=4.6Hz, H-2) 6.43(d, 1H, J=2.0Hz, H-9) 6.56(d, d, 1H, J=2.0Hz, J=7.9Hz, H-7) 7.32-7.47(m, 5H, arom) 7.64(d, 1H, J=7.9Hz, H-6) |

TABLE 1-continued

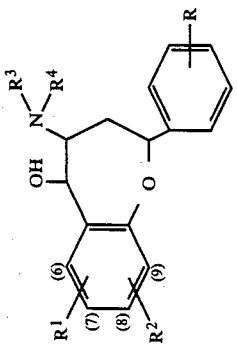

| Exp. No. (Comp. No.) | Substituent R1 | R2 | R3 | R4 | R5 | Melting Point (°C.) (Appearance) | IR Spectrum | NMR Spectrum |
|---|---|---|---|---|---|---|---|---|
| 11 (11d) | H | OH (8) | H | H | H | 159–161 | 3300, 3050, 2920 1620, 1590, 1500 1470, 1355, 1295 1160, 1120, 1045 995, 970, 750 695 | 1.83(m, 1H, H-3α)2.21(m, 1H, H-3β) 3.98(m, 1H, H-4)5.23(d, 1H, J=7.3Hz, H-5) 5.23(d, 1H, J=7.3Hz, H-5) 5.28(dd, 1H, J=2.6Hz, J=12.3Hz, H-2) 6.09(d, 1H, J=2.0Hz, H-9) 6.60(dd, 1H, J=2.0Hz, J=8.6Hz, H-7) 7.20–7.41(m, 6H, arom) |
| 12 (12a) | H | H | H | N—CH3 (piperidine) | H | (oil) | 3250, 2950, 2800 1600, 1570, 1480 1450, 1290, 1220 1140, 1045, 1010 795, 760, 700 | 2.31(s, 3H, N—CH3) 2.27–2.95(m, 10H, H-3, 2', 3', 5', 6') 3.15(m, 1H, H-4) 5.06(d, 1H, J=10.5Hz, H-5) 5.23(dd, 1H, J=7.3Hz, J=3.0Hz, H-2) 6.92–7.73(m, 9H, arom) |
| 12 (12b) | H | H | H | N—CH3 (piperidine) | H | 155–157 | 3400, 2920, 2800 1600, 1480, 1450 1280, 1240, 1220 1140, 1040, 1005 970, 930, 755 695 | 2.28(s, 3H, N—CH3) 2.12–2.90(m, 10H, H-3, 2', 3', 5', 6') 3.01(m, 1H, H-4) 5.18(d, 1H, J=4.9Hz, H-5) 5.30(dd, 1H, J=6.4Hz, J=3.8Hz, H-2) 7.00–7.48(m, 9H, arom) |
| 13 (13a) | H | H | H | —CH3 | H | 130.5–138.5 | 3000, 2850, 1600 1480, 1450, 1225 1010, 715, 760 700 | 1.76(br, s, 2H, OH, NH) 2.33–2.39(m, 2H, H-3) 2.51(s, 3H, N—CH3)3.25(m, 1H, H-4) 4.91–4.97(m, 1H, H-2 or 5) 5.22(s, 1H, H-2 or 5) 6.98–7.53(m, 9H, arom) |
| 13 (13b) | H | H | H | —CH3 | H | 177.0–177.5 | 3260, 2840, 1600 1575, 1480, 1450 1270, 1220, 1050 970, 780, 760 700, 675 | 1.80(br, s, 2H, OH, NH) 2.17(m, 1H, H-3α)2.55(s, 3H, NCH3) 2.57(m, 1H, H-3β)3.21(m, 1H, H-4) 4.96(d, 1H, J=7.2Hz, H-2 or 5) 5.16(dd, 1H, J=2.0Hz, J=9.9Hz, H-2 or 5) 7.30–7.48(m, 8H, arom) |
| 13 (13c) | H | H | H | —CH3 | H | 192–194 | 3300, 3070, 3040 1600, 1580, 1480 | 2.10(m, 1H, H-3α)2.46(m, 1H, H-3β) 2.48(s, 3H, NCH3)3.30(br, s, 1H, OH) |

TABLE 1-continued

Structure: chromane/benzopyran skeleton with OH, NR³R⁴ substituents on positions bearing R¹ (position 7), R² (position 8), and R⁵ on the phenyl group; positions labeled (6), (7), (8), (9).

| Exp. No. (Comp. No.) | R¹ | R² | R³ | R⁴ | R⁵ | Melting Point (°C.) (Appearance) | IR Spectrum | NMR Spectrum |
|---|---|---|---|---|---|---|---|---|
| 13 (13d) | H | H | H | —CH₃ | H | 172–173 | 1460, 1260, 1220 1110, 1050, 950 760, 730, 695 | 4.58(d, 1H, J=11.2Hz, H-5) 4.70(d, 1H, J=9.2Hz, H-2) 6.97–7.49(m, 8H, arom)7.70(m, 1H, H-6) 2.03(br.s., 2H, OH, NH) 2.23(m, 1H, H-3α)2.37(m, 1H, H-3β) 2.54(s, 3H, N—CH₃)3.03(m, 1H, H-4) 4.87(dd, 1H, J=2.0Hz, J=11.2Hz, H-2) 4.93(d, 1H, J=2.0Hz, H-5) 7.00–7.49(m, 9H, arom) |
| 14 (14a) | H | H | —CH₃ | —CH₃ | H | 65–66 | 3250, 2950, 1600 1570, 1480, 1450 1220, 1060, 1040 935, 750, 695 | 2.16(m, 1H, H-3α)2.34(m, 1H, H-3β) 2.37(s, 6H, 2xN—CH₃)3.13(m, 1H, H-4) 4.98(d, 1H, J=10.9Hz, H-5) 5.18(dd, 1H, J=10.9Hz, J=3.2Hz, H-2) 6.90–7.72(m, 9H, arom) |
| 14 (14b) | H | H | —CH₃ | —CH₃ | H | (oil) | 3300, 2930, 1600 1570, 1480, 1450 1240, 1220, 1040 970, 925, 755 | 2.12–2.35(m, 2H, H-3) 2.27(s, 6H, 2xN—CH₃) 2.97(m, 1H, H-4) 5.18(d, 1H, J=3.8Hz, H-5) 5.36(dd, 1H, J=6.4Hz, J=4.5Hz, H-2) 7.00–7.50(m, 9H, arom) |
| 14 (14c) | H | H | —CH₃ | —CH₃ | H | (oil) | 3230, 2940, 2890 2780, 1600, 1580 1480, 1455, 1260 1225, 1055, 1040 940, 760, 700 | 2.17–2.26(m, 2H, H-3) 2.37(s, 6H, N—CH₃)2.64(m, 1H, H-4) 3.10(br, s, 1H, OH) 4.57(dd, 1H, J=3.3Hz, J=9.9Hz, H-2 or 5) 4.82(d, 1H, J=9.2Hz, H-2 or 5) 6.96–7.48(m, 8H, arom) 7.79–7.82(m, 1H, H-6) |
| 14 (14d) | H | H | —CH₃ | —CH₃ | H | 173.5–174.0 | 3030, 2900, 2850 2780, 1595, 1570 1480, 1440, 1220 1050, 990, 780 680 | 1.58(br, s, 1H, OH)2.06(m, 1H, H-3α) 2.42(s, 6H, N—CH₃)2.56(m, 1H, H—3β) 3.17(m, 1H, H-4) 4.99(d, 1H, J=11.0Hz, H-2 or 5) 5.10(d, 1H, H-2 or 5) 6.97–7.47(m, 9H, arom) |
| 15 (15a) | H | H | H | —CH(CH₃)₂ | H | 227–228 | 3300, 3050, 3020 2950, 2920, 1600 1570, 1480, 1450 1220, 1150, 755 | 0.99(d, 3H, J=5.9Hz, —CH₃) 1.05(d, 3H, J=5.9Hz, —CH₃) 1.92(m, 1H, H-3α)2.56(m, 1H, H-3β) 2.70(br, s, 1H, OH) |

TABLE 1-continued

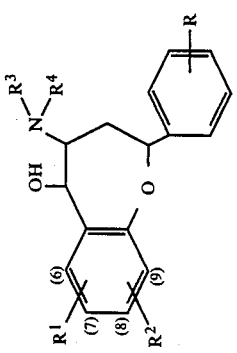

| Exp. No. (Comp. No.) | Substituent | | | | | Melting Point (°C.) (Appearance) | IR Spectrum | NMR Spectrum |
|---|---|---|---|---|---|---|---|---|
| | R¹ | R² | R³ | R⁴ | R⁵ | | | |
| 15 (15b) | H | H | H | —CH(CH$_3$)$_2$ | H | (oil) | 3300, 3020, 2950 1600, 1570, 1480 1450, 1380, 1220 1170, 1040, 970 905, 760, 730 690 | 1.01(d, 3H, J=2.0Hz, CH$_3$) 1.03(d, 3H, J=2.6Hz, CH$_3$) 2.15–2.36(m, 2H, H-3) 2.80(br, s, 1H, OH) 2.92(m, 1H, N—CH(CH$_3$)$_2$) 3.33(m, 1H H-4) 4.91(dd, 1H, J=9.9Hz, J=2.6Hz H-5) 5.08(d, 1H, J=2.6Hz, H-2) 6.97–7.53(m, 9H, arom) 2.92(m, 1H, N—CH(CH$_3$)$_2$) 3.21(m, 1H, H-4) 4.75(d, 1H, J=7.9Hz, H-5) 5.10(dd, 1H, J=11.2Hz, J=2.0Hz, H-2) 6.95–7.53(m, 9H, arom) |
| 16 (16b) | H | H | H | —CH$_2$—C$_6$H$_5$ | H | | 3300, 3030, 3000 2850, 1590, 1570 1475, 1440, 1220 1040, 1020, 740 690 | 2.03(m, 1H, H-3α)2.52(m, 1H, H-3β) 3.22(m, 1H, H-4) 3.82(dd, 2H, J=13.2Hz, J=25.7Hz, H-1') 4.79(d, 1H, J=7.2Hz, H-2 or 5) 5.16(dd, 1H, J=2.0Hz, J=11.2Hz, H-2 or 5) 6.98–7.40(m, 14H, arom) |
| 16 (16c) | H | H | H | —CH$_2$—C$_6$H$_5$ | H | 124.0–125.5 | 3030, 2820, 1600 1580, 1480, 1455 1430, 1380, 1260 1220, 1100, 1050 950, 770, 750 690 | 2.06(m, 1H, H-3α)2.11(br, s, 2H, OH, NH) 2.54(m, 1H, H-3β)2.70(m, 1H, H-4) 3.78(d, 1H, J=12.5Hz, H-1'α) 4.00(d, 1H, J=12.4Hz, H-1'β) 4.59(dd, 1H, J=1.3Hz, J=11.2Hz, H-2 or 5) 4.76(d, 1H, J=9.2Hz, H-2 or 5) 6.98–7.47(m, 13H, arom) 7.76–7.79(m, 1H, H-6) |

TABLE 1-continued

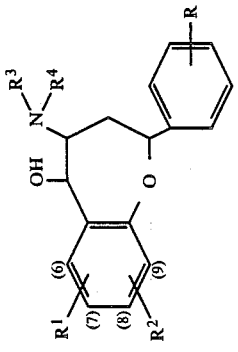

| Exp. No. (Comp. No.) | Substituent | | | | | Melting Point (°C.) (Appearance) | IR Spectrum | NMR Spectrum |
|---|---|---|---|---|---|---|---|---|
| | $R^1$ | $R^2$ | $R^3$ | $R^4$ | $R^5$ | | | |
| 17 (17a) | H | H | H | —(CH$_2$)$_2$—Ph | H | 121.5–122.0 | 3280, 3070, 2950 2850, 1615, 1580 1495, 1460, 1365 1300, 1260, 1240 1125, 1075, 1000 945, 765, 755 700 | 2.13–2.31(m, 2H, H-3) 2.62–2.97(m, 4H, H-1', 2') 3.25(m, 1H, H-4) 4.69(dd, 1H, J=3.3Hz, J=9.9Hz, H-2 or 5) 5.07(d, 1H, J=2.0Hz, H-2 or 5) 6.93–7.37(m, 13H, arom) 7.49(m, 1H, H-6) |
| 17 (17b) | H | H | H | —(CH$_2$)$_2$—Ph | H | 94.5–95.0 | 3300, 3060, 3020 2920, 2850, 1600 1580, 1480, 1450 1220, 1115, 1050 750, 700 | 1.97(m, 1H, H-3α)2.51(m, 1H, H-3β) 2.69–2.99(m, 4H, H-1', 2') 3.18(m, 1H, H-4) 4.75(d, 1H, J=7.91Hz, H-2 or 5) 4.96(dd, 1H, J=2.0Hz, 11.9Hz, H-2 or 5) 6.94–7.42(m, 14H, arom) |
| 17 (17c) | H | H | H | —(CH$_2$)$_2$—Ph | H | (oil) | 3260, 3050, 3000 2900, 2830, 1600 1570, 1475, 1440 1255, 1220, 1100 1040, 760, 690 | 1.7(br, s, 2H, OH, NH) 2.03(m, 1H, H-3α)2.45(m, 1H, H-3β) 2.53–2.90(m, 4H, H-1', 2') 3.11(m, 1H, H-4) 4.57(d, 1H, J=11.9Hz, H-2 or 5) 4.65(d, 1H, J=9.2Hz, H-2 or 5) 6.96–7.44(m, 13H, arom) 7.77(m, 1H, H-6) |
| 17 (17d) | H | H | H | —(CH$_2$)$_2$—Ph | H | 195.5–197 | 3250, 3000, 2880 1595, 1575, 1480 1445, 1240, 1220 1100, 1040, 985 760, 690 | 2.12–2.37(m, 4H, OH, NH, H-3) 2.74–2.90(m, 2H, H-2') 2.96–3.01(m, 2H, H-1') 3.12(m, 1H, H-4) 4.87(dd, 1H, J=1.3Hz, J=10.5Hz, H-2 or 5) 4.88(s, 1H, H-2 or 5) 6.97–7.44(m, 14H, arom) |

TABLE 1-continued

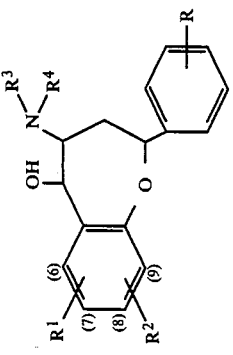

| Exp. No. (Comp. No.) | Substituent R¹ | R² | R³ | R⁴ | R⁵ | Melting Point (°C.) (Appearance) | IR Spectrum | NMR Spectrum |
|---|---|---|---|---|---|---|---|---|
| 18 (18b) | H | H | H | —(CH₂)₃—〔phenyl〕 | H | (oil) | 3270, 3050, 3010 2920, 2840, 1595 1575, 1480, 1445 1220, 1105, 1040 740, 690 | 1.73–1.84(m, 2H, H-2') 1.98(m, 1H, H-3α) 2.24(br. s, 2H, OH, NH) 2.47–2.78(m, 5H, H-3β, 1', 3') 3.14(m, 1H, H-4) 4.78(d, 1H, J=7.2Hz, H-2 or 5) 5.06(dd, 1H, J=0.8Hz, J=11.9Hz, H-2 or 5) 6.97–7.43(m, 14H, arom) |
| 18 (18c) | H | H | H | —(CH₂)₃—〔phenyl〕 | H | (oil) | 3270, 3010, 2920 2840, 1595, 1575 1475, 1445, 1260 1220, 1100, 1040 940, 900, 755 690 | 1.73–1.92(m, 2H, H-2') 2.03(m, 1H, H-3α) 2.43–2.72(m, 5H, H-3β, H-1', 3') 2.86(m, 1H, H-4) 4.56(d, 1H, J=11.2Hz, H-2 or 5) 4.66(d, 1H, J=8.6Hz, H-2 or 5) 6.97–7.45(m, 13H, arom) 7.78(m, 1H, H-6) |
| 19 (19c) | H | H | H | —CH₂—〔pyridyl〕 | H | 140–141 | 3400, 3050, 1580 1480, 1450, 1420 1260, 1220, 1060 950, 765, 695 | 2.14(m, 1H, H-3α) 2.27(br, s, 3H, OH, NH) 2.57(m, 1H, H-3β)2.71(m, 1H, H-4) 3.79(d, 1H, J=13, 2Hz, H-1'α) 4.02(d, 1H, J=13.2Hz, H-1'β) 4.62(d, 1H, J=9.9Hz, H-2 or 5) 4.77(d, 1H, J=9.2Hz, H-2 or 5) 6.99–7.77(m, 11H, arom) 8.53–8.57(m, 2H, H-2'', 6'') |
| 20 (20c) | H | H | H | —(CH₂)₂—〔p-OCH₃-phenyl〕 | —OCH₃ (p) | (oil) | 3260, 2900, 2830 1660, 1605, 1580 1505, 1450, 1245 1225, 1170, 1105 1035, 940, 820 760, 720 | 2.05(m, 1H, H-3α)2.39(m, 1H, H-3β) 2.53–3.14(m, 5H, H-1', 2', 4) 3.77(s, 3H, OCH₃)3.81(s, 3H, OCH₃) 4.51(d, 1H, J=11.2Hz, H-2 or 5) 4.66(d, 1H, J=9.2Hz, H-2 or 5) 6.76–7.35(m, 11H, arom) 7.75(m, 1H, H-6) |

TABLE 1-continued

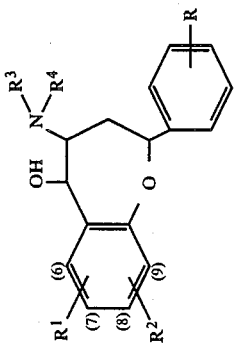

| Exp. No. (Comp. No.) | Substituent R¹ | R² | R³ | R⁴ | R⁵ | Melting Point (°C.) (Appearance) | IR Spectrum | NMR Spectrum |
|---|---|---|---|---|---|---|---|---|
| 21 (21c) | H | H | H | —(CH₂)₃— phenyl | —OCH₃ (p) | (oil) | 3400, 3100, 1600 1570, 1515, 1480 1445, 1240, 1220 1180, 1055, 1030 960, 825, 750 | 1.75–1.86(m, 2H, H-2) 2.06(m, 1H, H-3α)2.37(m, 1H, H-3β) 2.47–3.00(m, 7H, H-1', 3', 4, OH, NH) 3.76(s, 3H, OCH₃) 4.45(d, 1H, J=10.6Hz, H-2 or 5) 4.67(d, 1H, J=9.9Hz, H-2 or 5) 6.84–7.30(m, 12H, arom) 7.69(m, 1H, H-6) |
| 22 (22a) | H | Cl (8) | H | —(CH₂)₂— phenyl | H | (oil) | 1595, 1565, 1580 1450, 1365, 1220 1080, 980, 930 755, 740, 690 (HCl salt) | 1.60–2.04(m, 4H, OH, OH, H-3α, H-3β) 2.51–2.78(m, 4H, CH₂—CH₂) 3.05(m, 1H, H-4) 4.43(dd, 1H, J=9.8Hz, 3.3Hz, H-2) 4.85(d, 1H, J=2.0Hz, H-5) 6.78–7.25(m, 13H, Ar) |
| 23 (23a) | H | Cl | H | —(CH₂)₃— phenyl | H | (oil) | 3300, 3000–2700 1600, 1485, 1455 1220, 1080, 980 745, 695 (HCl salt) | 1.79(m, 2H, CH₂—CH₂—CH₂) 1.90–2.33(m, 4H, NH, OH, H-3α, H-3β) 2.48–2.78(m, 4H, CH₂—CH₂—CH₂) 3.21(m, 1H, H-4) 4.78(dd, 1H, J=9.9Hz, 3.3Hz, H-2) 5.02(d, 1H, J=2.0Hz, H-5) 7.02(s, 1H, H-9)7.10–7.45(m, 12H, Ar) |
| 24 (24b) | H | H | H | —(CH₂)₂— phenyl | —CO₂CH₃ (p) | (oil) | | 1.99(m, 1H, H-3α) 2.28(bs, 2H, OH, NH)2.47(m, 1H, H-3β) 2.78(m, 2H, OH═Ar)2.95(m, 2H, N—CH₂)mx,l 3.21(m, 1H, H-4)3.94(s, 3H, CO₂CH₃) 4.77(d, 1H, J=7.9Hz, H-5) 5.04(dd, 1H, J=11.2Hz, 2.0Hz, H-2) 6.98(dd, 1H, J=7.9Hz, 1.3Hz, H-9) 7.05–7.40(m, 7H, Ar) 7.43(d, 2H, J=7.9Hz, H-3') 8.04(d, 2H, J=7.9Hz, H-3') |

TABLE 1-continued

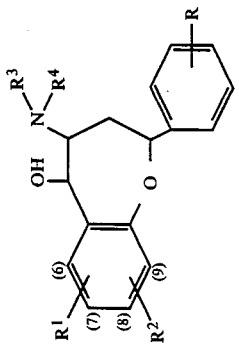

| Exp. No. (Comp. No.) | Substituent | | | | | Melting Point (°C.) (Appearance) | IR Spectrum | NMR Spectrum |
|---|---|---|---|---|---|---|---|---|
| | $R^1$ | $R^2$ | $R^3$ | $R^4$ | $R^5$ | | | |
| 25 (25b) | H | H | H | —(CH$_2$)$_4$— (phenyl) | H | (oil) | 3300, 3000, 2900 2850, 1600, 1570 1480, 1440, 1220 1040, 840, 690 | 1.41–1.70(m, 4H, H-2', 3') 2.05(m, 1H, H-3α) 2.40(br, s, 2H, OH, NH) 2.45–2.83(m, 5H, H-3, 1', 4') 3.18(m, 1H, H-4) 4.86(d, 1H, J=7.9Hz, H-2 or 5) 5.12(dd, 1H, J=9.2Hz, J=2.0Hz, H-2 or 5) 6.92–7.49(m, 14H, arom) |
| 25 (25c) | H | H | H | —(CH$_2$)$_4$— (phenyl) | H | (oil) | 3250, 2920, 2850 1600, 1580, 1480 1450, 1260, 1220 1110, 1045, 760 695 | 1.43–1.74(m, 4H, H-2', 3') 2.07(m, 1H, H-3α) 2.45–2.65(m, 5H, H-3β, 1', 4') 2.85(m, 1H, H-4) 4.57(d, 1H, J=11.2Hz, H-2 or 5) 4.65(d, 1H, J=9.2Hz, H-2 or 5) 6.97–7.46(m, 13H, arom) 7.78(m, 1H, H-6) |
| 26 (26a) | H | H | H | —(CH$_2$)$_2$— (4-OCH$_3$-phenyl) | H | 102–104 (colorless crystal) | 3270, 2950, 2900 1610, 1510, 1485 1255, 1220, 1025 985, 760 | 1.35(b, 2H, OH, NH) 2.20(m, 1H, H-3α)2.26(m, 1H, H-β) 2.59–2.95(m, 4H, CH$_2$CH$_2$) 3.25(m, 1H, H-4) 3.77(s, 3H, OCH$_3$) 4.66(dd, 1H, J=9.9Hz, 3.3Hz, H-2) 5.08(d, 1H, J=2.0Hz, H-5) 6.78(d, 2H, J=8.6Hz, H-3') 6.96(dd, 1H, J=7.9Hz, 1.3Hz, H-9) 7.03(d, 2H, J=8.6Hz, H-2') 7.10–7.38(m, 7H, arom) 7.50(dd, 1H, J=7.3Hz, 1.3Hz, H-6) |

TABLE 1-continued

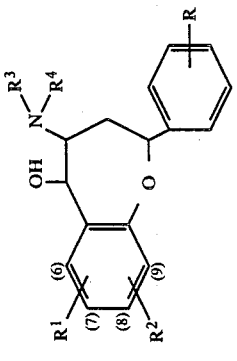

| Exp. No. (Comp. No.) | Substituent | | | | | Melting Point (°C.) (Appearance) | IR Spectrum | NMR Spectrum |
|---|---|---|---|---|---|---|---|---|
| | $R^1$ | $R^2$ | $R^3$ | $R^4$ | $R^5$ | | | |
| 26 (26b) | H | H | H | —(CH$_2$)$_2$—⟨OCH$_3$⟩ | H | 78-79 (colorless crystal) | 3200, 2930, 2800 1605, 1580, 1510 1450, 1455, 1240 1215, 1040, 960 740 | 1.99 (m, 1H, H-3α)2.54(m, 1H, H-3β) 2.71(m, 2H, ArCH$_2$)2.90(m, 2H, NH—CH$_2$) 3.20(m, 1H, H-4)3.78(s, 3H, OCH$_3$) 4.76(d, 1H, J=7.3Hz, H-5) 4.96(dd, 1H, J=11.5Hz, 2.3Hz, H-2) 6.80(d, 2H, J=8.8Hz, H-3') 6.96(d, 1H, J=7.9Hz, H-9) 7.06(d, 2H, J=8.8Hz, H-2') 7.08-7.42(m, 8H, arom) |
| 26 (26c) | H | H | H | —(CH$_2$)$_2$—⟨OCH$_3$⟩ | H | (oil) | 3300-2800, 1600 1575, 1480, 1440 1230, 1170, 1100 1020, 940, 810 760 | 2.01(m, 1H, H-3α)2.42(m, 1H, H-3β) 2.53-2.83(m, 4H, CH$_2$CH$_2$) 3.05(m, 1H, H-4)3.78(s, 3H, OCH$_3$) 4.55(dd, 1H, J=11.2Hz, 1.3Hz, H-2) 4.64(d, 1H, J=9.2Hz, H-5) 6.83(d, 2H, J=8.6Hz, H-3') 6.98(m, 1H, H-9) 7.80(d, 2H, J=8.6Hz, H-2') 7.18(m, 2H, H-7, H-8) 7.31-7.44(m, 5H, arom) 7.78(dd, 1H, J=4.0Hz, 1.3Hz, H-6) |
| 27 (27a) | H | H | H | —(CH$_2$)$_2$—⟨OH⟩ | H | (colorless amorphous) | 3400-2900, 1600 1510, 1480, 1450 1220, 1100, 1040 820, 760 | 2.15-2.33(m, 2H, H-3α, H-3β) 2.55-2.94(m, 4H, CH$_2$—H$_2$) 3.25(m, 1H, H-4) 3.79(b, s, 2H, OH, NH) 4.76(dd, 1H, J=7.9Hz, 2.0Hz, H-2) 5.08(s, 1H, H-4) 6.65(d, 2H, J=7.9Hz, H-3') 6.91(d, 2H, J=7.9Hz, H-2') 6.93(m, 1H, H-9) 7.05-7.19(m, 2H, H-7, H-8) 7.25-7.43(m, 7H, arom, OH) |

TABLE 1-continued

[Structure shown: bicyclic benzofuran-type scaffold with OH, NR³R⁴ substituents, R¹ at position (6)/(7), R² at position (8)/(9), and a phenyl group with R substituent attached via O]

| Exp. No. (Comp. No.) | R¹ | R² | R³ | Substituent R⁴ | R⁵ | Melting Point (°C.) (Appearance) | IR Spectrum | NMR Spectrum |
|---|---|---|---|---|---|---|---|---|
| 27 (27b) | H | H | H | —(CH₂)₂—C₆H₄—OH (para) | H | (colorless amorphous) | 3400–2900, 1600 1520, 1485, 1460 1220, 1100, 1040 820, 750, 700 | 1.99(m, 1H, H-3α)2.53(m, 1H, H-3β) 2.69(m, 2H, ArCH₂) 2.80–3.10(m, 4H, NH—CH₂, OH) 3.20(m, 1H, H-4) 4.77(d, 1H, J=7.9Hz, H-5) 4.97(dd, 1H, J=11.2Hz, 2.0Hz, H-2) 6.69(d, 2H, J=8.6Hz, H-3') 6.75–7.09(m, 4H, H-2', H-7, H-9) 7.14–7.40(m, 7H, arom) |
| 27 (27c) | H | H | H | —(CH₂)₂—C₆H₄—OH (para) | H | (colorless amorphous) | 3400–2900, 1610 1520, 1480, 1450 1220, 1100, 1040 820, 760, 700 | 1.60b, 2H, OH, NH) 2.02(m, 1H, H-3α)2.43(m, 1H, H-3β) 2.53–2.82(m, 4H, CH₂—CH₂) 3.05(m, 1H, H-4) 4.56(d, 1H, J=11.2Hz, H-2) 4.65(d, 1H, J=9.9Hz, H-5) 6.75(d, 2H, J=8.6Hz, H-3') 6.98(m, 1H, H-9) 7.05(d, 2H, J=8.6Hz, H-2') 7.18(m, 2H, H-7, H-8) 7.30–7.41(m, 6H, arom) 7.76(m, 1H, H-6) |
| 28 (28b) | H | H | H | —(CH₂)₂—C₆H₃(OCH₃)₂ (3,4-dimethoxy) | H | | 3250, 2950, 2850 1600, 1580, 1500 1480, 1450, 1260 1230, 1150, 1135, 1020, 775, 720 690 | 2.02(br, s, 2H, OH, NH) 2.58(m, 1H, H-3α) 2.75–3.09(m, 5H, H—3β, 1', 2') 3.28(m, 1H, H-4) 3.82(s, 3H, OCH₃) 3.85(s, 3H, OCH₃) 4.91(d, 1H, J=7.9Hz, H-2 or 5) 5.02(dd, 1H, J=2.6Hz, J=11.9Hz, H-2 or 5) 6.68–7.47(m, 12H, arom) |

TABLE 1-continued

Structure:

R³R⁴N group and OH on central chain, with phenyl ring (R substituted) on one side and benzofuran-type ring bearing R¹ (6,7), R² (8,9) on the other.

| Exp. No. (Comp. No.) | Substituent R¹ | R² | R³ | R⁴ | R⁵ | Melting Point (°C.) (Appearance) | IR Spectrum | NMR Spectrum |
|---|---|---|---|---|---|---|---|---|
| 28 (28c) | H | H | H | —(CH₂)₂— (2-OCH₃, 4-OCH₃ phenyl) | H | — | 3270, 2920, 2820 1600, 1580, 1505 1450, 1260, 1220 1150, 1135, 1020 900, 760, 720 670 | 2.08(m, 1H, H-3α)2.43(m, 1H, H-3β) 2.56–2.84(m, 4H, H-1', 2') 3.06(m, 1H, H-4)3.65(br, s, 1H, NH) 3.83(s, 3H, OCH₃)3.84(s, 3H, OCH₃) 4.56(d, 1H, J=9.9Hz, H-2 or 5) 4.79(d, 1H, J=19.7Hz, H-2 or 5) 6.70–7.43(m, 11H, arom) 7.77(m, 1H, H-6) |
| 29 (29a) | H | H | H | —(CH₂)₂— (2-OH, 4-OH phenyl) | H | (colorless amorphous) | 3400–2900, 1600 1480, 1220, 1120 1050, 760 | 2.15–2.35(m, 2H, H-3α, H-3β) 2.58(m, 2H, ArCH₃)2.91(m, 2H, N—CH₃) 3.29(m, 1H, H-4) 4.49(b, 4H, NH, OH, Ar—OH) 4.83(dd, 1H, J=9.6Hz, 3.3Hz, H-2) 5.12(s, 1H, H-5) 6.35(d, 1H, J=1.3Hz, H-2') 6.51(dd, 1H, J=7.9Hz, 1.3Hz, H-6') 6.75(d, 1H, J=9.6Hz, H-9) 6.92(d, 1H, J=7.9Hz, H-5') 7.00(m, 1H, H-7)7.15(m, 1H, H-8) 7.25–7.39(m, 6H, arom) |
| 29 (29b) | H | H | H | —(CH₂)₂— (2-OH, 4-OH phenyl) | H | (colorless amorphous) | 3400–2900, 1600 1480, 1450, 1220 1110, 1040, 750 695 | 2.07(m, 1H, H-3α) 2.48–2.66(m, 3H, H-3β, ArCH₃) 2.89(m, 1H, N—CH₃)3.01(m, 1H, N—CH) 3.21(m, 1H, H-4) 4.77(d, 1H, J=6.6Hz, H-5) 4.90(dd, 1H, J=12.5Hz, 1.3Hz, H-2) 6.42(s, 1H, H-2') 6.57(d, 1H, J=7.9Hz, H-5') 6.79(d, 1H, J=7.9Hz, H-6') 6.94(d, 1H, J=7.3Hz, H-9) 7.02(m, 1H, H-7) 7.17–7.38(m, 9H, arom, x2OH) |

TABLE 1-continued

[Structure: chroman-type compound with R¹ at position 7, R² at position 8, positions 6 and 9 marked, with OH and NR³R⁴ substituents on the saturated ring, and a phenyl group bearing R substituent]

| Exp. No. (Comp. No.) | Substituent R¹ | R² | R³ | R⁴ | R⁵ | Melting Point (°C.) (Appearance) | IR Spectrum | NMR Spectrum |
|---|---|---|---|---|---|---|---|---|
| 29 (29c) | H | H | H | —(CH₂)₂—[2,4-dihydroxyphenyl] | H | (colorless amorphous) | 3500–3300, 1605 1460, 1265, 1230 1120, 1050, 950 765, 700 | 2.07(m, 1H, H-3α)2.42(m, 1H, H-3β) 2.57–2.81(m, 4H, 2x—CH₂) 3.05(m, 3H, NH, OH, H-4) 4.57(dd, 1H, J=11.2Hz, 1.2Hz, H-5) 4.71(d, 1H, J=9.9Hz, H-5) 6.60(dd, 1H, J=7.9Hz, 2.0Hz, N—6') 6.69(d, 1H, J=2.0Hz, H-2') 6.77(d, 1H, J=7.9Hz, H-5') 6.98(dd, 1H, J=7.9Hz, 1.3Hz, H-9) 7.16(m, 2H, H-7, H-8) 7.29–7.43(m, 5H, arom) 7.69(dd, 1H, J=5.8Hz, 2.0Hz, H-6) |
| 30 (30b) | H | H | H | —(CH₂)₂—[3-pyridyl] | H | (oil) | 3500–3300 3100–2500, 1600 1550, 1480, 1450 1220, 1060, 760 700 (HCl salt) | 1.96(m, 1H, H-3α)2.52(m, 1H, H-3β) 2.74(t, 2H, J=6.6Hz, ArCH₂) 2.94(m, 2H, N—CH₃) 3.18(m, 1H, H-4) 4.79 (d, 1H, J=9.4Hz, H-5) 5.05(dd, 1H, J=11.2Hz, 2.0Hz, H-2) 6.98(dd, 1H, J=7.9Hz, 1.3Hz, H-9) 7.03–7.41(m, 9H, Ar, H-5') 7.46(ddd, 1H, J=7.9Hz, 2.0Hz, 2.0Hz, H-3')8.41(m, 2H, H-2', H-6') |
| 30 (30c) | H | H | H | —(CH₂)₂—[3-pyridyl] | H | (oil) | 3400–3200 3000–2600, 1600 1480, 1450, 1225 1060, 795, 760 700, 680 (HCl salt) | 2.05(m, 1H, H-3α) 2.45(ddd, 1H, J=14.9Hz, 3.3Hz, 2.0Hz, H-3β)2.60–2.88(m, 4H, CH₂CH₂) 3.13(m, 1H, H-4) 4.58(dd, 1H, J=11.2Hz, 1.3Hz, H-2) 4.67(d, 1H, J=9.9Hz, H-5) 6.99(m, 1H, H-9) 7.12–7.46(m, 8H, arom)7.51(m, 1H, H-4') 7.75(dd, 1H, J=5.9Hz, 3.3Hz, H-6) 8.47(m, 2H, H-6', H-2') |

TABLE 1-continued

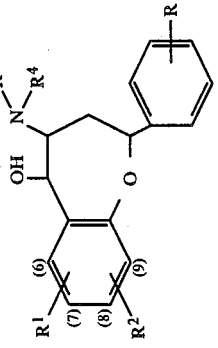

| Exp. No. (Comp. No.) | Substituent R[1] | R[2] | R[3] | R[4] | R[5] | Melting Point (°C.) (Appearance) | IR Spectrum | NMR Spectrum |
|---|---|---|---|---|---|---|---|---|
| 31 (31b) | H | H | —CH₃ | —(CH₂)₂—C₆H₅ | H | (oil) | 3250, 3010, 2950 2850, 1600, 1570 1480, 1450, 1220 1045, 755, 700 | 2.81–2.37(m, 2H, H-3)2.42(s, 3H, NCH₃) 2.64–2.91(m, 4H, H-1′, 2′) 3.26(m, 1H, H-4) 4.97(d, 1H, J=9.9Hz, H-2 or 5) 5.16(dd, 1H, J=4.6Hz, J=11.2Hz, H-2 or 5) 6.90–7.42(m, 13H, arom) 7.72(d, 1H, J=7.9Hz, H-6) |
| 31 (31c) | H | H | —CH₃ | —(CH₂)₂—C₆H₅ | H | (oil) | 3250, 3000, 2930 2830, 1600, 1570 1480, 1445, 1260 1220, 1050, 945 760, 695 | 2.13–2.36(m, 2H, H-3)2.41(s, 3H, NCH₃) 2.61–2.94(m, 5H, H-4, 1′, 2′) 4.55(dd, 1H, J=2.0Hz, J=10.6Hz, H-2 or 5) 4.83(d, 1H, J=9.9Hz, H-2 or 5) 6.94–7.53(m, 13H, arom) 7.78(m, 1H, H-6) |
| 32 (32b) | H | H | —CH₃ | —(CH₂)₃—C₆H₅ | H | (oil) | 3200, 3020, 2930 2850, 1600, 1570 1480, 1450, 1220 1040, 940, 750 695 | 1.75–1.89(m, 2H, H-2) 2.13–2.72(m, 6H, H-3, 1′, 3′) 2.35(s, 3H, NCH₃)3.24(m, 1H, H-4) 4.99(d, 1H, J=10.5Hz, H-2 or 5) 5.16(dd, 1H, J=4.6Hz, J=11.2Hz, H-2 or 5) 6.90–7.44(m, 13H, arom) 7.74(d, 1H, J=7.9Hz, H-6) |
| 32 (32c) | H | H | —CH₃ | —(CH₂)₃—C₆H₅ | H | (oil) | 3250, 3050, 3020 2940, 2850, 1600 1575, 1480, 1450 1225, 1045, 760 725, 695 | 1.79–1.91(m, 2H, H-2′) 2.10–2.75(m, 7H, H-3, 4, 1′, 3′) 2.33(s, 3H, NCH₃) 4.55(dd, 1H, J=1.3Hz, J=10.5Hz, H-2 or 5)4.85(d, 1H, J=9.2Hz, H-2 or 5) 5.50(br, s, 1H, OH) 6.96–7.56(m, 13H, arom) 7.82(m, 1H, H-6) |

TABLE 1-continued
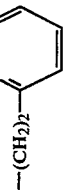
| Exp. No. (Comp. No.) | Substituent | | | | | Melting Point (°C.) (Appearance) | IR Spectrum | NMR Spectrum |
|---|---|---|---|---|---|---|---|---|
| | $R^1$ | $R^2$ | $R^3$ | $R^4$ | $R^5$ | | | |
| 33 (33c) | H | H | H | —(CH$_2$)$_2$—(2-pyridyl) | H | | | 2.10(m, 1H, H-3α)2.35(br, s, 2H, OH, NH) 2.50(m, 1H, H-3β)2.63(m, 1H, H-4) 2.97–3.04(m, 2H, H-1') 3.35(m, 1H, H-2'α)3.50(m, 1H, H-2'β) 4.58(d, 1H, J=11.2Hz, H-2 or 5) 4.73(d, 1H, J=9.9Hz, H-2 or 5) 6.98–7.83(m, 12H, arom)8.53(m, 1H, H-3'') |

Starting compounds used in the Examples are prepared according to the procedures described in the following Reference Examples.

REFERENCE EXAMPLE 1

2-phenyl-2,3,4,5-tetrahydro-1-benzoxepin-5-one (compound R1)

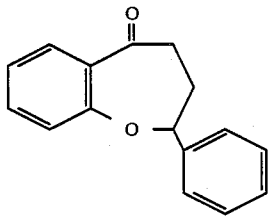

4.49 g (19 m moles) of 3,4-benzo-5-oxo-1-phenyl-2-oxabicyclo-[4,1,0]heptane was dissolved in 200 ml of benzene. 6.06 g (1.1 equivalent amount) of tri-n-butyltin hydride and 1.75 g (0.55 equivalent amount) of azobisisobutylonitrile were added to the solution, and the whole was heated to reflux for one hour. After cooling, the reaction mixture was washed with water and dried with anhydrous magnesium sulfate. After filtrating off the magnesium sulfate, the filtrate was concentrated to obtain a residue, which was then applied to a silica gel column, and eluted with a mixture of hexane/ethyl acetate (95:5) to obtain 5.88 g (yield 87.5%) of the desired compound.

REFERENCE EXAMPLE 2

4-hydroxyimino-2-phenyl-2,3,4,5-tetrahydro-1-benzoxepin-5-one (compound R2)

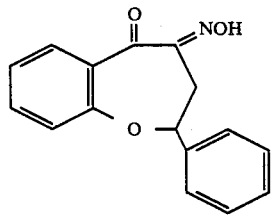

5.36 g (22.5 m moles) of 2-phenyl-2,3,4,5-tetrahydro-1-benzoxepin-5-one (compound R1 of Reference Example 1) was dissolved in a mixture of 130 ml of tetrahydrofuran and 230 ml of ethyl ether, and 13.4 ml of hydrogen chloride-saturated ethyl ether was added to the solution, which was then cooled to −20° C. 5.79 ml (49.5 m moles) of sodium butylnitrite was added dropwise to the solution, and the reaction mixture was allowed to stand at −15° C. to −20° C. for two days. A saturated sodium chloride aqueous solution was added to the reaction mixture to separate the phases. An organic phase was obtained, washed with water, and dried with anhydrous magnesium sulfate. After filtrating off the magnesium sulfate, the filtrate was concentrated, and the concentrate was washed with hexane and dried to obtain 5.46 g (yield 90.8%) of the desired compound.

REFERENCE EXAMPLE 3

4-acetamido-2-phenyl-2,3,4,5-tetrahydro-1-benzoxepin-5-one (R3a, R3b)

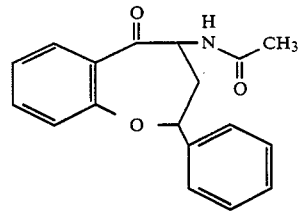

308 mg (1.15 m moles) of 4-hydroxyimino-2-phenyl-2,3,4,5-tetrahydro-1-benzoxepin-5-one (compound R2 of Reference Example 2) was dissolved in 23 ml of acetic anhydride, 280 mg (3.75 equivalent amount) of zinc powder was added to the solution, and then 0.658 ml (10 equivalent amount) of acetic acid was added dropwise at a room temperature. The reaction mixture was stirred at a room temperature for 3 hours and concentrated. The residue was dissolved in ethyl acetate and the solution was filtrated to eliminate the zinc powders. The filtrate was washed with sodium bicarbonate aqueous solution and then with water, and dried with anhydrous magnesium sulfate. After filtrating off the magnesium sulfate, the filtrate was concentrated to obtain a residue, which was then applied to a silica gel column, and eluted with a mixture of hexane/ethyl acetate (7:3) to obtain 137 mg (yield 40.3%) of a mixture of stereoisomers R3a and R3b (ratio 1:1) of the desired compound.

REFERENCE EXAMPLE 4

4-acetamido-5-hydroxy-2-phenyl-2,3,4,5-tetrahydro-1-benzoxepin (R4a, R4b, R4c)

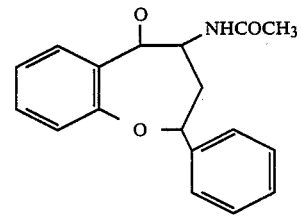

797 mg (2.70 m moles) of 4-acetamido-2-phenyl-2,3,4,5-tetrahydro-1-benzoxepin (compound R3a of Reference Example) was dissolved in 50% methanol, 411 mg (10.8 m moles) of sodium borohydride was added to the solution at −50° C. to −20° C., and the whole was stirred for 5 hours. The reaction mixture was concentrated, and ice water was added to the concentrate. The mixture was extracted with methylene chloride, and the extract was washed with water and dried with anhydrous magnesium sulfate. After filtrating off the magnesium sulfate, the filtrate was concentrated to obtain a residue, which was then applied to a silica gel column, and eluted with a mixture of methylene chloride/methanol (98:2) to obtain stereoisomers R4a (22.5 mg; yield 28.0%) and R4b (485 mg; yield 60.4%) of the desired compound.

Stereoisomer R3b of Reference Example 3 was treated according to the same procedure as described above, to obtain stereoisomer R4c of the desired compound almost selectively (yield 85%).

REFERENCE EXAMPLE 5 TO 13

According to the same procedures as described in Reference Examples 1, 2, 3, and 4, corresponding oxabicycloheptane derivatives were treated to obtain compounds of Reference Examples 5 to 13.

REFERENCE EXAMPLE 14

4-bromo-2-phenyl-2,3,4,5-tetrahydro-1-benzoxepin-5-one (R14)

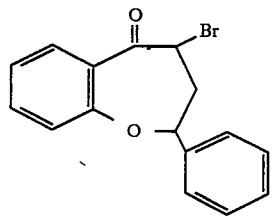

800 mg (3.36 m moles) of 2-phenyl-2,3,4,5-tetrahydro-1-benzoxepin-5-one (compound R1 of Reference Example 1) was dissolved in 80 ml of absolute ethyl ether, and 808 mg (1.5 equivalent amount) of bromine was added to the solution dropwise over 15 minutes under ice-cooling. The reaction mixture was washed with a sodium sulfate aqueous solution followed by water, and then dried with anhydrous magnesium sulfate. After filtrating off the magnesium sulfate, the filtrate was concentrated to obtain a residue, which was then applied to a silica gel column, and eluted with a mixture of hexane/ethyl acetate (98:2) to obtain 1.02 g (yield 95.7%) of the desired compound in a form of a diastereomer mixture (R14a and R14b, ratio 3:1).

REFERENCE EXAMPLE 15

4-(4-methylpiperazinyl)-2-phenyl-2,3,4,5-tetrahydro-1-benzoxepin-5-one (R15a, R15b)

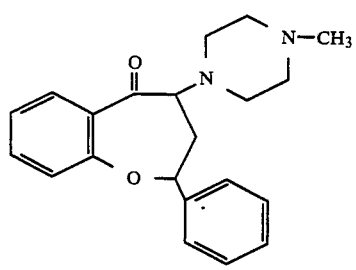

970 mg (3.1 m moles) of 4-bromo-2-phenyl-2,3,4,5-tetrahydro-1-benzoxepin-5-one (compound R14 of Reference Example 14) was dissolved in 100 ml of benzene, 3.1 g (10 equivalent amount) of N-methylpiperazine was added to the solution, and the whole was heated to reflux for 7 hours. After distilling off the solvent, water was added to the residue, and the mixture was extracted with methylene chloride. The organic phase was washed with water and dried with anhydrous magnesium sulfate. After filtrating off the magnesium sulfate, the filtrate was concentrated to obtain a residue, which was then applied to a silica gel column, and eluted with a mixture of methylene chloride/methanol (90:10) to obtain diastereomers R15a (700 mg; yield 55.1%) and R15b (220 mg; yield 17.3%) of the desired compound.

REFERENCE EXAMPLES 16 TO 18

According to the same procedure as described in Reference Example 15, compounds of Reference Examples 16 to 18 were obtained. Details of the properties of these compounds are set forth in Table 2.

REFERENCE EXAMPLE 19

5-hydroxy-4-(4-phenyl)butyrlamido-2-phenyl-2,3,4,5-tetrahydro-1-benzoxepin (R19b, R19c)

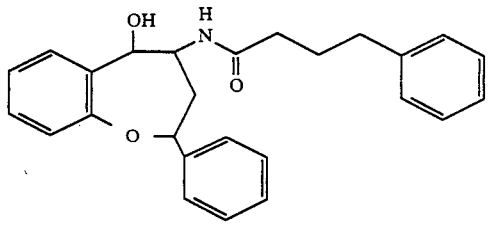

200 mg (0.784 m moles) of 4-amino-5-hydroxy-2-phenyl-2,3,4,5-tetrahydro-1-benzoxepin (compound 1b of Example 1) was dissolved in 50 ml of methylene chloride, 155 mg (0.941 m moles) of 4-phenylbutyric acid and 180 mg (0.94 m moles) of 1-ethyl-3-(3-dimethylaminopropyl) carbodiimide hydrochloride were added to the solution, and the whole was stirred for 17 hours at room temperature. The reaction mixture was washed with water and dried with anhydrous magnesium sulfate. After filtrating off the magnesium sulfate, the filtrate was concentrated to obtain a residue, which was then applied to a silica gel column, and eluted with a mixture of methylene chloride/methanol (97:3) to obtain 281 mg (yield 93.1%) of the desired compound (R19b).

Stereoisomer 1c was treated according to the same procedure as described above to obtain stereoisomer R19a of the desired compound (yield 93.7%).

REFERENCE EXAMPLES 20 TO 24

Compounds of Example 1 were treated according to the same procedure as described in Reference Example 19 to obtain compounds of Reference Examples 20 to 24. The properties of these compounds are set forth in Table 3.

REFERENCE EXAMPLE 25

9-phenyl-9,10,10a,3a-tetrahydro-[1]-benzoxepino[4,5-d]oxazolidin-2-one (R25a, R25b, R25c, R25d)

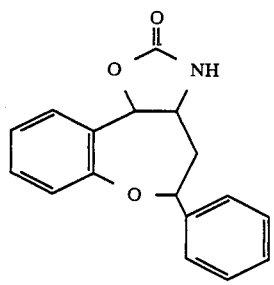

200 mg (0.784 m moles) of 4-amino-5-hydroxy-2-phenyl-2,3,4,5-tetrahydro-1-benzoxepin (compound 1a of Example 1) was dissolved in 30 ml of benzene, 127 mg (0.784 m moles) of carbonyldiimidazole was added to the solution, and the whole was stirred for 3 hours with heating. After distilling off the solvent, the residue was applied to a silica gel column, and eluted with a mixture of methylene chloride/methanol (99:1) to obtain 158 mg (71.7%) of the desired compound R25a.

Each of stereoisomers 1b, 1c, and 1d was treated according to the same procedure as described above to obtain stereoisomers R25b, R25c, and R25d of the desired compound.

REFERENCE EXAMPLE 26

1-phenethyl-9-phenyl-9,10,10a,3a-tetrahydro-[1]-benzoxepino[4,5-d]oxazolidin-2-one

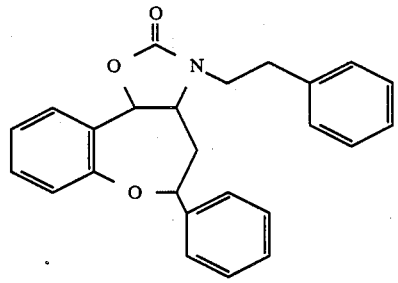

235 mg (0.84 m moles) of 9-phenyl-9,10,10a,3a-tetrahydro-[1]-benzoxepino[4,5-d]oxazolidin-2-one (compound R25b of Reference Example 25) was dissolved in 40 ml of dioxane, 100 mg (2.51 m moles; 60% suspension in oil) was added to the solution, and the whole was stirred at 110° C. for 30 minutes under heating. After cooling, 10 ml of dimethyl sulfoxide and 0.343 ml (2.51 m moles) of phenethyl bromide were added to the reaction mixture, which was then stirred for 2 hours. After distilling off the solvent, ice-water was added to the reaction mixture, which was then extracted with ethyl ether. The extract was washed with water, and dried with anhydrous magnesium sulfate. After filtrating off the magnesium sulfate, the filtrate was concentrated to obtain a residue which was then applied to a silica gel column, and eluted with a mixture of hexane/ethyl acetate (8:2) to obtain 266 mg (yield 82.6%) of the desired compound R26b.

Stereoisomer R25c of Reference Example 25 was treated according to the same procedure as described above to obtain stereoisomer R26c of the desired compound.

REFERENCE EXAMPLES 27 TO 29

Compounds of Reference Example 25 were treated according to the same procedure as described in Reference Example 26 to obtain compounds of Reference Examples 27 to 29.

Physico-chemical properties of the compounds prepared in Reference Examples 1 to 29 are set forth in the following Tables 2, 3, and 4.

TABLE 2

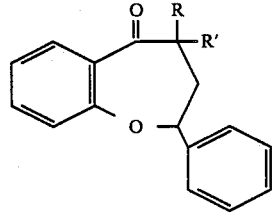

| Ref. Exp. No. (Comp. No.) | R and R' | Melting Point (°C.) (Appearance) | IR Spectrum | NMR Spectrum |
|---|---|---|---|---|
| 1 | H<br>H | (oil) | 3060, 2930, 1690, 1600<br>1475, 1455, 1290, 1225<br>760, 700 | 2.43 (m, 2H, H—3')<br>2.82 (m, 1H, H—4α) 3.16 (m, 1H, H—4β)<br>5.08 (dd, 1H, J=8.14 Hz, J=9.0 Hz, H—2)<br>7.10 (m, 2H, arom)<br>7.30–7.50 (m, 5H, arom)<br>7,82 (dd, 1H, J=8.57 Hz, J=2.57 Hz, H—6) |
| 2 | =N—OH | 126–128 | 3250, 3040, 2960, 1670<br>1600, 1480, 1460, 1310<br>1260, 1220, 1150, 1050<br>930, 890, 750, 695 | 3.29 (dd, 1H, J=17.6 Hz, J=1.7 Hz, H—3α)<br>3.52 (dd, 1H, J=17.6 Hz, J=9.9 Hz, H—3β)<br>5.37 (dd, 1H, J=1.7 Hz, J=9.9 Hz, H—2)<br>7.01–7.52 (m, 8H, arom)<br>8.00 (dd, 1H, J=7.2 Hz, J=1.1 Hz, H—6) |
| 3 (R3a) | H<br>—NHCOCH3 | 181–183 | 3300, 3050, 2920, 1700<br>1650, 1600, 1550, 1470<br>1460, 1370, 1355, 1275<br>1220, 1100, 1055, 1020<br>960, 950, 910, 785<br>755, 695 | 2.05 (s, 3H, CH3)<br>2.09 (m, 1H, H—3α) 3.30 (m, 1H, H—3β)<br>4.94 (dd, 1H, J=12.5 Hz, J=4.6 Hz, H—4)<br>5.33 (m, 1H, H—2)<br>6.67 (m, 1H, NH)<br>7.11–7.51 (m, 8H, arom)<br>7.86 (dd, 1H, J=7.9 Hz, J=2.0 Hz, H—6) |
| 3 (R3b) | H<br>—NHCOCH3 | 119–121 | 3370, 3060, 2930, 1680<br>1670, 1600, 1500, 1460<br>1320, 1200, 1060, 990<br>790, 695 | 2.07 (s, 3H, CH3)<br>2.26 (m, 1H, H—3α) 2.81 (m, 1H, H—3β)<br>5.07 (m, 1H, H—4)<br>5.63 (dd, 1H, J=11.9 Hz, J=5.3 Hz, H—2)<br>6.80–7.51 (m, 8H, arom)<br>7.98 (dd, 1H, J=7.9 Hz, J=2.0 Hz, H—6) |
| 14 | H<br>Br | (oil) | 3050, 3020, 1690, 1600<br>1470, 1450, 1270, 1220<br>1150, 1100, 1050, 1010<br>920, 755, 690 | 2.71 and 3.01–3.10 (m, H—3)<br>4.88 (dd, J=5.9 and 4.6 Hz, H—4)<br>5.06 (dd, J=11.9 and 4.3 Hz, H—4)<br>5.16–5.22 (m, H—2)<br>7.01–7.86 (m, arom) |

TABLE 2-continued

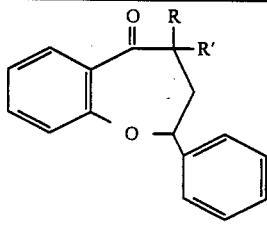

| Ref. Exp. No. (Comp. No.) | R and R' | Melting Point (°C.) (Appearance) | IR Spectrum | NMR Spectrum |
|---|---|---|---|---|
| 15 (R15a) | -N(CH₂CH₂)₂N—CH₃, H | (oil) | 3050, 2920, 2790, 1690 1600, 1570, 1470, 1450 1270, 1220, 1165, 1140 1020, 950, 920, 750 690 | 2.33 (s, 3H, N—CH₃) 2.30–2.80 (m, 10H, H—3, H—2', 3', 5', 6') 3.90 (dd, 1H, J=9.5 Hz, J=7.3 Hz, H—4) 5.02 (dd, 1H, J=11.7 Hz, J=4.3 Hz, H—2) 7.08–7.77 (m, 9H, arom) |
| 15 (R15b) | -N(CH₂CH₂)₂N—CH₃, H | | | 2.37 (s, 3H, N—CH₃) 2.30–2.80 (m, 10H, H—3, 2', 3', 5', 6') 3.92 (dd, 1H, J=9.9 Hz, J=6.9 Hz, H—4) 5.02 (dd, 1H, J=12.1 Hz, J=4.3 Hz, H—2) 7.05–7.80 (m, 9H, arom) |
| 16 | H, -NH—CH₃ | (oil) | | 2.12 (m, 1H, H—3α) 2.40 (s, 3H, N—CH₃) 3.96 (m, 1H, H—3β) 4.01 (dd, 1H, J=10.9 Hz, J=7.7 Hz, H—4) 5.92 (dd, 1H, J=12.2 Hz, J=4.5 Hz, H—2) 6.86–7.84 (m, 9H, arom) |
| 17 (R17a) | H, -N(CH₃)₂ | (oil) | 3050, 2920, 1690, 1600 1470, 1450, 1275, 1220 1150, 1100, 950, 920 755, 695 | 2.42 (s, 6H, 2 × N—CH₃) 2.49 (m, 1H, H—3α) 2.73 (m, 1H, H—3β) 3.87 (dd, 1H, J=10.3 Hz, J=7.7 Hz, H—4) 5.00 (dd, 1H, J=11.6 Hz, J=4.5 Hz, H—2) 7.07–7.80 (m, 9H, arom) |
| 17 (R17b) | H, -N(CH₃)₂ | (oil) | | 2.45 (s, 6H, 2 × N—CH₃) 2.49 (m, 1H, H—3α) 2.73 (m, 1H, H—3β) 3.76 (dd, 1H, J=7.7 Hz, J=4.5 Hz, H—4) 5.33 (dd, 1H, J=8.3 Hz, J=6.4 Hz, H—2) 7.07–7.87 (m, 9H, arom) |
| 18 (R18a) | H, -NH₂ | (oil) | | (as acetic acid salt) 2.08 (brs, 5H, NH₂, COCH₂) 2.47 (m, 1H, H—3α), 3.12 (m, 1H, H—3β) 4.72 (m, 1H, H—4) 4.98 (dd, 1H, J=11.0 Hz, J=4.4 Hz, H—2) 7.10–7.87 (m, 9H, arom) |
| 18 (18b) | H, -NH₂ | (oil) | | (as acetic acid salt) 2.06 (br, s, 5H, NH₂, COCH₃) 2.25 (m, 1H, H—3α) 2.85 (m, 1H, H—3β) 4.30 (m, 1H, H—4) 5.12 (m, 1H, H—2) 7.03–7.60 (m, 8H, arom) 7.92 (m, 1H, H—6) |

TABLE 3

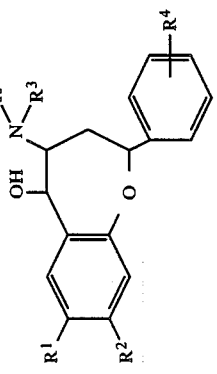

| Ref. Exp. No. (Comp. No.) | Substituent | | | | Melting Point (°C.) (Appearance) | IR Spectrum | NMR Specturm |
|---|---|---|---|---|---|---|---|
| | $R^1$ | $R^2$ | $R^3$ | $R^4$ | | | |
| 4 (R4a) | H | H | —COCH₃ | H | 155–157 | 3300, 2920, 1660 1530, 1490, 1450 1225, 1050, 1040 980, 770, 760 695 | 1.96(s, 3H, CH₃) 2.30(m, 1H, H-3α)2.52(m, 1H, H-3β) 4.13(d, 1H, J=5.9Hz, OH) 4.57(m, 1H, H-4) 4.75(dd, 1H, J=2.6Hz, J=11.9Hz, H-5) 5.31(d, 1H, J=5.3Hz, H-2) 5.49(m, 1H, NH) 7.02–7.56(m, 9H, arom) |
| 4 (R4b) | H | H | —COCH₃ | H | 176–178 | 3300, 3050, 2920 1640, 1540, 1480 1450, 1370, 1210 1050, 980, 760 695 | 1.97(s, 3H, CH₃) 2.18(m, 1H, H-3α)2.75(m, 1H, H-3β) 3.03(d, 1H, J=7.9Hz, OH) 4.62(m, 1H, H-4) 4.77(dd, 1H, J=7.3Hz, J=6.6Hz, H-5) 4.85(d, 1H, J=11.2Hz, H-2) 5.31(m, 1H, NH) 7.06–7.48(m, 9H, arom) |
| 4 (R4c) | H | H | —COCH₃ | H | 171–173 | 3360, 3050, 2920 1620, 1550, 1480 1450, 1370, 1350 1230, 1050, 970 950, 770, 695 | 1.95(s, 3H, CH₃) 2.20(m, 1H, H-3α)2.51(m, 1H, H-3β) 3.29(d, 1H, J=6.6Hz, OH) 4.25(m, 1H, H-4) 4.99(m, 2H, H-2, H-5) 5.77(m, 1H, NH) 7.01–7.61(m, 9H, arom) |
| 5 (R5a) | —OCH₃ | H | —COCH₃ | H | | 3250, 3050, 2900 1640, 1540, 1485 1370, 1260, 1240 1200, 1140, 1035 980, 880, 815 755, 735, 695 | 1.94(s, 3H, COCH₃) 2.15–2.29(m, 1H, H-3α) 2.41–2.53m, 1H, H-3β) 3.80(s, 3H, OCH₃)4.46(br, s, 1H, OH) 4.56–4.58(m, 1H, H-4) 4.62(d, 1H, J=11.9Hz, H-2 or 5) 5.30(s, 1H, H-2 or 5) 5.60(d, 1H, J=5.9Hz, NH) 6.71–7.43(m, 8H, arom) |
| 5 (R5b) | —OCH₃ | H | —COCH₃ | H | | 3550, 3270, 2950 2900, 1635, 1560 1495, 1475, 1280 1200, 1145, 1080 1040, 960, 880 825, 700 | 1.97(s, 3H, COCH₃) 2.09–2.16(m, 1H, H-3α) 2.61–2.72(m, 1H, H-3β) 3.42(br, s, 1H, OH)3.77(s, 3H, OCH₃) 4.52–4.60(m, 1H, H-4) 4.72(s, 1H, H-2 or 5) |

TABLE 3-continued

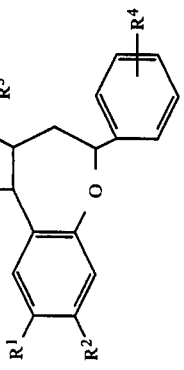

| Ref. Exp. No. (Comp. No.) | Substituent | | | | Melting Point (°C.) (Appearance) | IR Spectrum | NMR Spectrum |
|---|---|---|---|---|---|---|---|
| | $R^1$ | $R^2$ | $R^3$ | $R^4$ | | | |
| 5 (R5c) | —OCH$_3$ | H | —COCH$_3$ | H | | 3550, 3350, 3270 1635, 1560, 1495 1455, 1280, 1200 1145, 1080, 1040 955, 880, 825 760, 700 | 4.82(dd, 1H, J=1.3Hz, J=11.9Hz, H-2 or 5)5.57(d, 1H, J=7.9Hz, NH) 6.76—7.44(m, 8H, arom) 1.97 (s, 3H, COCH$_3$) 2.17—2.23(m, 1H, H-3α) 2.41—2.48(m, 1H, H-3β) 3.47(d, 1H, J=6.6Hz, OH) 3.82(s, 3H, OCH$_3$) 4.12—4.22(m, 1H, H-4) 4.83(dd, 1H, J=1.3Hz, J=9.9Hz, H-2 or 5)5.72(d, 1H, J=5.0Hz, NH) 6.73—7.48(m, 9H arom) |
| 6 (R6a) | H | —OCH$_3$ | —COCH$_3$ | H | 86—88 | 3300, 2950, 1640 1610, 1500, 1440 1280, 1195, 1160 1120, 1030, 985 735, 695 | 1.94(s, 3H COCH$_3$) 2.28(m, 1H, H-3α)2.43(m, 1H, H-3β) 3.75(s, 3H, OCH$_3$)4.24(br, s, 1H, OH) 4.50(m, 1H, H-4) 4.83(dd, 1H, J=2.62Hz, J=11.9Hz, H-5) 5.15(s, 1H, H-2) 5.78(d, 1H, J=6.4Hz, NH) 6.58(d, 1H, J=2.6Hz, H-9) 6.68(dd, 1H, J=2.6Hz, J=8.6Hz, H-7) 7.27—7.40(m, 6H arom) |
| 6 (R6b) | H | —OCH$_3$ | —COCH$_3$ | H | 164—166 | 3300, 2950, 1640 1610, 1490, 1440 1260, 1190, 1155 1110, 1030, 800 730, 690 | 1.93(s, 3H, COCH$_3$) 2.13(m, 1H, H-3α)2.73(m, 1H, H-3β) 3.17(d, 1H, J=5.9Hz, OH) 3.75(s, 3H, OCH$_3$)4.55(m, 1H, H-4) 4.66(m, 1H, H-5) 4.84(d, 1H, J=10.6Hz, H-2) 5.56(d, 1H, J=7.9Hz, NH) 6.61(d, 1H, J=2.6Hz, H-9) 6.64(dd, 1H, J=8.6Hz, J=2.6Hz, H-7) 7.19—7.41(m, 6H, arom) |
| 6 (R6c) | H | —OCH$_3$ | —COCH$_3$ | H | 152—154 | 3280, 2950, 1640 1610, 1550, 1500 1440, 1240, 1190 1160, 1110, 1040 1030, 740, 700 | 1.93(s, 3H, COCH$_3$) 2.17(m, 1H, H-3α)2.54(m, 1H, H-3β) 3.70(d, 1H, J=5.9Hz, OH) 3.75(s, 3H, OCH$_3$)4.27(m, 1H, H-4) 4.91(dd, 1H, J=5.3Hz, J=7.9Hz, H-5) |

TABLE 3-continued

[Structure: chromane/chroman ring with OH, NHR³ substituents, R¹ and R² on left benzene ring, R⁴ on right phenyl group, O in ring]

| Ref. Exp. No. (Comp. No.) | Substituent R¹ | R² | R³ | R⁴ | Melting Point (°C.) (Appearance) | IR Spectrum | NMR Spectrum |
|---|---|---|---|---|---|---|---|
| 7 (R7a) | H | Cl | —COCH₃ | H | | 3300, 3050, 2900 1640, 1600, 1560 1540, 1480, 1365 1290, 1215, 1080 1050, 1020, 980 900, 730, 690 | 5.03(d, 1H, J=2.6Hz, J=10.6Hz, H-2) 6.12(d, 1H, J=7.9Hz, NH) 6.56(d, 1H, J=2.6Hz, H-9) 6.69(dd, 1H, J=2.6Hz, J=7.9Hz, H-7) 7.27–7.45(m, 6H, arom) 1.94(s, 3H, CH₃) 2.26(m, 1H, H-3α)2.49(m, 1H, H-3β) 4.51(m, 1H, H-4.68(br, s, 1H, OH) 4.77(dd, 1H, J=2.0Hz, J=11.9Hz, H-5) 5.21(s, 1H, H-2) 5.69(d, 1H, J=7.2Hz, N—H) 7.05(d, 1H, J=2.0Hz, H-9) 7.13(dd, 1H, J=2.0Hz, J=7.9Hz, H-7) 7.28–7.49(m, 6H, arom) |
| 7 (R7b) | H | Cl | —COCH₃ | H | 200–201 | 3300, 1640, 1540 1480, 1400, 1370 1210, 1055, 985 805, 755, 695 | 1.99(s, 3H, CH₃) 2.11(m, 1H, H-3α)2.71(m, 1H, H-3β) 3.29(br, s, 1H, OH)4.53(m, 1H, H-4) 4.81(d, 1H, J=6.6Hz, H-5) 4.93(dd, 1H, J=12.4Hz, J=1.32Hz, H-2) 5.50(d, 1H, J=7.9Hz, NH) 7.06(d, 1H, J=2.0Hz, H-9) 7.11(dd, 1H, J=2.0Hz, J=7.9Hz, H-7) 7.14–7.51(m, 6H, arom) |
| 7 (R7c) | H | Cl | —COCH₃ | H | 214–215 | | 1.94(s, 3H, CH₃) 2.20(m, 1H, H-3α)2.49(m, 1H, H-3β) 3.78(br, s, 1H, OH)4.19(m, 1H, H-4) 4.90–4.97(m, 2H, H-5) 5.94(d, 1H, J=7.2Hz, N—H) 7.03–7.40(m, 7H, arom) 7.52(d, 1H, J=7.2Hz, H-6) |
| 8 (R8a) | —OCH₃ | —OCH₃ | —COCH₃ | H | | 3300, 2900, 2800 1640, 1610, 1530 1500, 1440, 1205 1190, 1120, 1110 1040, 1010 | 1.97(s, 3H, COCH₃) 2.23–2.32(m, 1H, H-3α) 2.42–2.538m, 1H, H-3β) 3.80(s, 3H, OCH₃)3.85(s, 3H, OCH₃) 4.52–4.58(m, 1H, H-4) 4.70(dd, 1H, J=2.0Hz, J=11.0Hz, H-2 or 5)5.24(s, 1H, H-2 or 5) 5.69(d, 1H, J=7.3Hz, NH) |

TABLE 3-continued

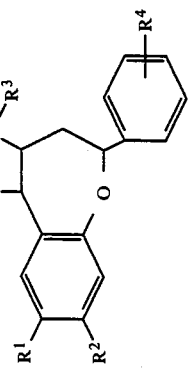

| Ref. Exp. No. (Comp. No.) | Substituent R[1] | R[2] | R[3] | R[4] | Melting Point (°C.) (Appearance) | IR Spectrum | NMR Spectrum |
|---|---|---|---|---|---|---|---|
| 8 (R8b) | —OCH₃ | —OCH₃ | —COCH₃ | H | | 3300, 3050, 2920 1640, 1610, 1500 1450, 1260, 1220 1190, 1110, 1040 1000, 970, 725 695 | 6.60s, 1H, H-9)7.07(s, 1H, H-6) 7.32–7.42(m, 5H, arom) 1.98(s, 3H, COCH₃) 2.11–2.18(m, 1H, H-3α) 2.68–2.79(m, 1H, H-3β) 3.05(br, s, 1H, OH)3.82(s, 3H, OCH₃) 3.88(s, 3H, OCH₃) 4.57–4.68(m, 2H, H-4, H-2 or 5) 4.80(dd, 1H, J=1.3Hz, J=10.6Hz, H-2 or 5)5.42(d, 1H, J=8.6Hz, NH) 6.62(s, 1H, H-9)6.81(s, 1H, H-6) |
| 8 (R8c) | —OCH₃ | —OCH₃ | —COCH₃ | H | | 3300, 2920, 2820 1640, 1610, 1540 1500, 1460, 1440 1260, 1210, 1190 1120, 1040, 1000 900, 720, 695 | 7.33–7.42(m, 5H, arom) 1.94(s, 3H, COCH₃) 2.10–2.22(m, 1H, H-3α) 2.44–2.52(m, 1H, H-3β) 3.81(s, 3H, OCH₃)3.88(s, 3H, OCH₃) 4.20–4.28(m, 1H, H-4) 4.88–4.94(m, 2H, H-2, 5) 6.03(d, 1H, J=7.9Hz, NH) 6.57(s, 1H, H-9)7.10(s, 1H, H-6) |
| 9 (R9a) | H | H | —COCH₃ | —OCH₃ (p) | | 3260, 3050, 2900 2820, 1640, 1600 1540, 1500, 1480 1450, 1365, 1300 1240, 1170, 1100 1080, 1030, 975 900, 820, 760 720 | 7.30–7.45(m, 5H, arom) 1.94(s, 3H, COCH₃) 2.21–2.30(m, 1H, H-3α) 2.47–2.58(m, 1H, H-3β) 3.82(s, 3H, OCH₃) 4.27(d, 1H, J=5.9Hz, OH) 4.53–4.58(m, 1H, H-4) 4.71(dd, 1H, J=1.3Hz, J=11.9Hz, H-2 or 5)5.28(d, 1H, J=3.9Hz, H-2 or 5)5.57(d, 1H, J=6.6Hz, NH) 6.90–7.36(m, 7H, arom) |
| 9 (R9b) | H | H | —COCH₃ | —OCH₃ (p) | | 3290, 3050, 2950 2900, 2820, 1640 1605, 1540, 1510 1480, 1440, 1370 1300, 1240, 1205 1170, 1050, 1030 | 7.53(dd, 1H, J=1.3Hz, J=7.2Hz, H-6) 1.96(s, 3H, COCH₃) 2.11–2.18(m, 1H, H-3α) 2.69–2.81(m, 1H, H-3β) 3.08(d, 1H, J=7.2Hz, OH) 3.83(s, 3H, OCH₃) 4.57–4.65(m, 1H, H-4) |

TABLE 3-continued

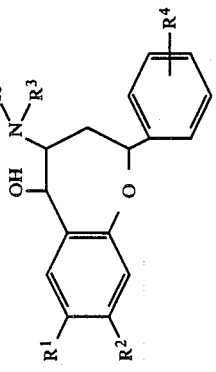

| Ref. Exp. No. (Comp. No.) | Substituent | | | | Melting Point (°C.) (Appearance) | IR Spectrum | NMR Specturm |
|---|---|---|---|---|---|---|---|
| | $R^1$ | $R^2$ | $R^3$ | $R^4$ | | | |
| 9 (R9c) | H | H | —COCH$_3$ | —OCH$_3$ (p) | | 980, 825, 780 | 4.75(d, 1H, J=7.2Hz, H-2 or 5) 4.81(dd, 1H, J=1.3Hz, J=11.9Hz, H-2 or 5)5.30-5.34(m, 1H, NH) 6.89-7.39(m, 8H, arom) |
| 10 (R10a) | H | H | —COCH$_3$ | | | 3250, 3050, 2930 2830, 1640, 1610 1580, 1550, 1510 1480, 1450, 1370 1300, 1240, 1220 1175, 1040, 940 820, 750 | 2.17(s, 3H, COCH$_3$) 2.15-2.27(m, 1H, H-3α) 2.44-2.52(m, 1H, H-3β) 3.23(d, 1H, J=5.9Hz, OH) 3.83(s, 3H, OCH$_3$) 4.23-4.27(m, 1H, H-4) 4.91(dd, 1H, J=2.0Hz, J=9.9Hz, H-2 or 5)5.01(dd, 1H, J=5.9Hz, J=8.6Hz, H-2 or 5) 5.79-5.82(m, 1H, NH) 6.91-7.39(m, 7H, arom) 7.59(d, 1H, J=6.6Hz, H-6) |
| 10 (R10b) | H | H | —COCH$_3$ | Cl (p) | | 3280, 3050, 2900 1640, 1540, 1480 1450, 1370, 1250 1220, 1085, 1045 1010, 980, 900 810, 760, 730 | 1.95(s, 3H, COCH$_3$) 2.25-2.33(m, 1H, H-3α) 2.38-2.49(m, 1H, H-3β) 4.12(br, s, 1H, OH) 4.51-4.57(m, 1H, H-4) 4.76(dd, 1H, J=2.6Hz, J=11.2Hz, H-2 or 5)5.26(s, 1H, H-2 or 5) 5.55(d, 1H, J=6.6Hz, NH) 7.00-7.40(m, 7H, arom) 7.53(dd, 1H, J=1.3Hz, J=7.3Hz, H-6) |
| 10 (R10c) | H | H | —COCH$_3$ | Cl (p) | | 3280, 3050, 2900 1640, 1540, 1480 1450, 1370, 1210 1190, 1155, 1005 980, 860, 780 | 1.97(s, 3H, COCH$_3$) 2.12-2.20(m, 1H, H-3α) 2.64-2.75(m, 1H, H-3β) 2.93(d, 1H, J=7.2Hz, OH) 4.57-4.65(m, 1H, H-4) 4.75(d, 1H, J=7.2Hz, H-2 or 5) 4.82(dd, 1H, J=2.0Hz, J=12.5Hz, H-2 or 5)5.28(d, 1H, J=7.9Hz, NH) 7.04-7.40(m, 8H, arom) |
| 10 (R10c) | H | H | —COCH$_3$ | Cl (p) | | 3250, 3050, 2950 1640, 1540, 1480 1365, 1220, 1080 | 1.99(s, 3H, COCH$_3$) 2.08-2.21(m, 1H, H-3α) 2.47-2.54(m, 1H, H-3β) |

TABLE 3-continued

| Ref. Exp. No. (Comp. No.) | Substituent | | | | Melting Point (°C.) (Appearance) | IR Spectrum | NMR Spectrum |
|---|---|---|---|---|---|---|---|
| | $R^1$ | $R^2$ | $R^3$ | $R^4$ | | | |
| 11 (R11a) | H | H | —COCH$_3$ | —CH$_3$ (p) | | 1040, 1010, 815 | 3.16(d, 1H, J=6.0Hz, OH) 4.21–4.32(m, 1H, H-4) 4.92(dd, 1H, J=1.7Hz, J=9.9Hz, H-2 or 5)4.95–5.02(m, 1H, H-2 or 5) 5.85(d, 1H, J=7.2Hz, NH) 6.99–7.41(m, 7H, arom) |
| 11 (R11b) | H | H | —COCH$_3$ | —CH$_3$ (p) | | 3300, 3000, 2900 1640, 1540, 1480 1450, 1250, 1220 970, 960, 750 | 7.58(dd, 1H, J=1.1Hz, J=6.1Hz, H-6) 1.91(s, 3H, COCH$_3$) 2.20–2.28(m, 1H, H-3α) 2.37(s, 3H, CH$_3$) 2.42–2.53(m, 1H, H-3β) 4.50–4.55(m, 1H, H-4) 4.72(dd, 1H, J=1.3Hz, J=11.9Hz, H-2 or 5)5.25(s, 1H, H-2 or 5) 5.73(d, 1H, J=14.7Hz, NH) 7.00–7.32(m, 7H, arom) |
| 11 (R11c) | H | H | —COCH$_3$ | —CH$_3$ (p) | | 3300, 1640, 1540 1480, 1375, 1210 1055, 980, 810 780 | 7.52(dd, 1H, J=1.2Hz, J=7.3Hz, H-6) 1.96(s, 3H, COCH$_3$) 2.11–2.20(m, 1H, H-3α) 2.37(s, 3H, CH$_3$) 2.69–2.81(m, 1H, H-3β) 3.04(d, 1H, J=7.9Hz, OH) 4.58–4.65(m, 1H, H-4) 4.75(d, 1H, J=7.2Hz, H-2 or 5) 4.81(d, 1H, J=11.9Hz, H-2 or 5) 5.29–5.31(m, 1H, NH) 7.04–7.36(m, 8H, arom) |
| | | | | | | 3250, 2900, 1640 1540, 1480, 1440 1360, 1220, 1040 960, 940, 800 750 | 1.96(s, 3H, COCH$_3$) 2.17–2.26(m, 1H, H-3α) 2.38(s, 3H, CH$_3$) 2.44–2.52(m, 1H, H-3β) 3.25(d, 1H, J=6.6Hz, OH) 4.22–4.27(m, 1H, H-4) 4.92(dd, 1H, J=2.6Hz, J=10.6Hz, H-2 or 5)5.02(dd, 1H, J=5.9Hz, J=8.6Hz, H-2 or 5) 5.75–5.79(m, 1H, NH) 6.99–7.39(m, 7H, arom) |

TABLE 3-continued

[Structure: chroman with R¹, R² on one ring; OH, NH-R³ substituents; phenyl with R⁴]

| Ref. Exp. No. (Comp. No.) | Substituent R¹ | R² | R³ | R⁴ | Melting Point (°C.) (Appearance) | IR Spectrum | NMR Spectrum |
|---|---|---|---|---|---|---|---|
| 12 (R12a) | H | H | —COCH₃ | —CF₃ (p) | | 3280, 3050, 2900 1640, 1550, 1485 1330, 1225, 1165 1120, 1070, 1020 980, 830, 760 735 | 7.59(dd, 1H, J=2.0Hz, J=7.9Hz, H-6) 1.94(s, 3H, CH₃) 2.27–2.46(m, 2H, H-3) 4.29(br, s, 1H, OH) 4.51–4.60(m, 1H, H-4) 4.85(dd, 1H, J=2.6Hz, J=10.6Hz, H-2 or 5) 5.25(s, 1H, H-2 or 5) 5.69(d, 1H, J=6.6Hz, NH) 7.00–7.66(m 8H, arom) |
| 12 (R12b) | H | H | —COCH₃ | —CF₃ (p) | | 3280, 3050, 2920 1645, 1545, 1480 1320, 1215, 1150 1115, 1070, 1060 985, 860, 830 780, 755 | 1.97(s, 3H, CH₃) 2.17–2.24(m, 1H, H-3α) 2.65–2.76(m, 1H, H-3β) 2.87–2.90(m, 1H, OH) 4.59–4.67(m, 1H, H-4) 4.77(dd, 1H, J=6.6Hz, J=9.3Hz, H-2 or 5)4.89(d, 1H, J=11.9Hz, H-2 or 5)5.27–5.30(m, 1H, NH) 7.06–7.67(m, 8H, arom) |
| 12 (R12c) | H | H | —COCH₃ | —CF₃ (p) | | 3250, 3070, 2900 2850, 1640, 1545 1480, 1445, 1370 1320, 1220, 1160 1120, 1110, 1060 1040, 825, 755 | 2.00(s, 3H, CH₃) 2.11–2.26(m, 1H, H-3α) 2.52–2.60(m, 1H, H-3β) 3.03(d, 1H, J=5.9Hz, OH) 4.24–4.36(m, 1H, H-4) 4.98–5.04(m, 2H, H-2, 5) 5.72–5.76(m, 1H, NH) 7.01–7.68(m, 8H, arom) |
| 13 (R13a) | H | H | —COCH₃ | —COOCH₃ (p) | (amorphous) | 3500–3100, 1720 1640, 1540, 1480 1280, 1220, 1110 1050, 980, 765 | 1.85(b, 1H, OH) 1.92(s, 3H, Ac) 2.24–2.45(m, 2H, H-3α, H-3β) 3.91(s, 3H, CO₂CH₃) 4.52(m, 1H, H-5) 4.86(dd, 1H, J=11.2Hz, 1.6Hz, H-2) 5.23(s, 1H, H-5) 5.83(d, 1H, J=7.3Hz, NH) 7.01(d, 1H, J=7.9Hz, H-9) 7.12–7.23(m, 2H, H-7, H-8) 7.47(d, 2H, J=11.9Hz, H-2′) |

TABLE 3-continued

Structure: phenyl-O-chromane with OH and NHR³ substituents, R¹/R² on one ring, R⁴ on the other.

| Ref. Exp. No. (Comp. No.) | Substituent R¹ | R² | R³ | R⁴ | Melting Point (°C.) (Appearance) | IR Spectrum | NMR Spectrum |
|---|---|---|---|---|---|---|---|
| 13 (R13b) | H | H | —COCH₃ | —COOCH₃ (p) | (amorphous) | | 7.50(m, 1H, H-6) 8.04(d, 2H, J=11.9Hz, H-3') 1.97(s, 3H, Ac) 2.05–2.22(m, 1H, H-3α) 2.68(m, 1H, H-3β) 3.92(s, 3H, CO₂CH₃)4.60(m, 1H, H-4) 4.78(d, 1H, J=6.6Hz, H-5) 4.92(d, 1H, J=11.9Hz, H-2) 5.49(d, 1H, J=7.9Hz, NH) 6.99–8.07(m, Ar) |
| 13 (R13c) | H | H | —COCH₃ | —COOCH₃ (p) | (amorphous) | | 1.96(s, 3H, Ac) 2.05–2.22(m, 1H, H-3α) 2.54(ddd, 1H, J=14.5Hz, 4.6Hz, 2.6Hz, H-3β)3.92(s, 3H, CO₂CH₃) 4.26(m, 1H, H-4)4.99(m, 2H, H-2, H-5) 6.07(d, 1H, J=7.9Hz, NH) 6.99–8.07(m, Ar) |
| 19 (R19b) | H | H | —CO(CH₂)₃—Ph | H | | 3050, 3020, 2920 1640, 1540, 1480 1455, 1210, 1050 980, 760, 695 | 1.84–2.02(m, 2H, H-3') 2.10–2.16(m, 2H, H-2') 2.57–2.78(m, 4H, H-3, H-4') 3.70(br, 1H, OH)4.59(m, 1H, H-4) 4.77(d, 1H, J=6.6Hz, H-2 or 5) 4.84(dd, 1H, J=1.3Hz, J=11.9Hz, H-2 or 5)5.41(d, 1H, J=7.9Hz, NH) 7.04–7.44(m, 14H, arom) |
| 19 (R19c) | H | H | —CO(CH₂)₃—Ph | H | | 3050, 3010, 2920 2840, 1645, 1550 1485, 1450, 1230 1040, 970, 760 735, 695 | 1.84–1.94(m, 2H, H-3') 2.10–2.23(m, 3H, H-2', H-3α) 2.51(m, 1H, H-3β) 2.57–2.62(m, 2H, H-4') 3.34(br, s, 1H, OH)4.26(m, 1H, H-4) 4.96–5.05(m, 2H, H-2, H-5) 5.73(m, 1H, H-6) 7.04–7.47(m, 13H, arom) 7.59(dd, 1H, J=2.0Hz, J=7.3Hz, H-6) |

TABLE 3-continued

Structure: R¹, R² on one benzene ring with OH and NHR³ substituents on a chain connected via O to another benzene ring bearing R⁴.

| Ref. Exp. No. (Comp. No.) | R¹ | R² | Substituent R³ | R⁴ | Melting Point (°C.) (Appearance) | IR Spectrum | NMR Spectrum |
|---|---|---|---|---|---|---|---|
| 20 (R20a) | H | H | —COCH₂—(C₆H₄)—OCH₃ (p) | H | (oil) | 3300, 2900, 1640 1500, 1240, 1030 900, 820, 760 695 | 2.15(m, 1H, H-3α)2.41(m, 1H, H-3β) 3.44(s, 2H, CH₂Ar)3.78(s, 3H, OCH₃) 4.28(d, 1H, J=11.9Hz, H-5) 4.46(m, 1H, H-4)5.38(m, 2H, H-2, NH) 6.75(d, 2H, J=9.2Hz, H-3') 6.87(d, 2H, J=9.2Hz, H-2') 6.95(dd, 1H, J=7.9Hz, 1.3Hz, H-9) 7.1–7.5(m, 8H, arom) |
| 20 (R20b) | H | H | —COCH₂—(C₆H₄)—OCH₃ (p) | H | 160–162 | 3270, 1635, 1500 1215, 1200, 1180 1020, 885 | 2.12(m, 1H, H-3α)2.68(m, 1H, H-3β) 3.46(s, 2H, CH₂Ar)3.77(s, 3H, OCH₃) 4.45(d, 1H, J=11.2Hz, H-5) 4.57(m, 2H, H-2, H-4)5.08(m, 1H, NH) 6.73(d, 2H, J=8.6Hz, H-3') 6.95(d, 2H, H-7, H-8) 7.2–7.4(m, 7H, arom) |
| 20 (R20c) | H | H | —COCH₂—(C₆H₄)—OCH₃ (p) | H | 169–171 | 3250, 1640, 1505 1240, 1220, 1040 760 | 2.06(m, 1H, H-3α)2.50(m, 1H, H-3β) 3.48(ss, 2H, CH₂Ar)3.80(s, 3H, OCH₃) 4.24(m, 1H, H-4)4.93(m, 2H, H-2, H-5) 5.75(m, 1H, NH) 6.82(d, 2H, J=8.6Hz, H-3') 6.95(dd, 1H, J=7.9Hz, 1.3Hz, H-9) 7.05(d, 2H, J=8.6Hz, H-2') 7.1–7.4(m, 7H, arom)7.53(m, 1H, H-6) |
| 21 (R21a) | H | H | —COCH₂—(C₆H₄)—OH (p) | H | 154–156 | 3500–2700, 1625 1500, 1220, 1040 820, 760 | 2.16(m, 1H, H-3α)2.36(m, 1H, H-3β) 3.39(s, 2H, CH₂Ar)4.36(m, 1H, H-5) 4.46(m, 2H, H-2, H-4) 5.23(s, 1H, Ar—OH) 5.53(d, 1H, J=7.3Hz, NH) 6.60(d, 2H, J=8.6Hz, H-3') 6.79(d, 2H, J=8.6Hz, H-2') 6.93(dd, 1H, J=7.9Hz, 1.3Hz, H-9) 7.09(m, 1H, H-7)7.19(m, 1H, H-8) 7.25–7.38(m, 6H, arom) |

TABLE 3-continued

[Structure: chromanone-type skeleton with OH, NHR³ substituents on a benzopyran fused to phenyl ring with R¹, R² on one ring and R⁴ on the other]

| Ref. Exp. No. (Comp. No.) | Substituent | | | | Melting Point (°C.) (Appearance) | IR Spectrum | NMR Spectrum |
|---|---|---|---|---|---|---|---|
| | R¹ | R² | R³ | R⁴ | | | |
| 21 (R21b) | H | H | —COCH₂—⟨C₆H₄⟩—OH (para) | H | 189–190 | 3500–2900, 1640, 1500, 1480, 1440, 1210, 1040, 745 | 2.04(ddd, 1H, J=15.2Hz, 4.0Hz, 1.3Hz, H-3α)2.67(m, 1H, H-3β) 3.42(s, 2H, CH₂Ar)4.44(m, 1H, H-4) 4.55(d, 1H, J=11.2Hz, H-2) 4.63(d, 1H, J=6.6Hz, H-5) 6.67(d, 2H, J=7.9Hz, H-2') 6.90(d, 2H, J=7.9Hz, H-3') 6.97(d, 1H, J=7.9Hz, H-9) 7.03–7.13(m, 2H, H-7, H-8) 7.22–7.40(m, 6H, arom) |
| 21 (R21c) | H | H | —COCH₂—⟨C₆H₄⟩—OH (para) | H | 225–227 | 3500–2900, 1640, 1525, 1510, 1480, 1440, 1260, 1225, 1040, 755, 695 | 2.07(ddd, 1H, J=13.9Hz, 11.2Hz, 7.3Hz, H-3α)2.53(ddd, 1H, J=13.9Hz, 4.6Hz, 2.6Hz, H-3β)3.41(s, 2H, CH₂Ar) 4.17(m, 1H, H-4) 4.88(d, 1H, J=8.6Hz, H-5) 4.97(dd, 1H, J=11.2Hz, 2.6Hz, H-2) 6.73(d, 2H, J=8.6Hz, H-3') 6.94(dd, 1H, J=7.9Hz, 1.3Hz, H-9) 6.95(d, 2H, J=8.6Hz, H-2') 7.10–7.24(m, 2H, H-7, H-8) 7.30–7.38(m, 5H, arom) 7.48(d, 1H, J=7.9Hz, H-6) |
| 22 (R22b) | H | H | —COCH₂—⟨C₆H₃⟩(OCH₃)(OCH₃) | H | | 3350, 3050, 2940, 2840, 1640, 1600, 1590, 1515, 1455, 1420, 1260, 1215, 1155, 1025, 995, 760, 700 | 2.14(m, 1H, H-3α)2.68(m, 1H, H-3β) 3.47(d, 2H, J=3.9Hz, H-2') 3.78(s, 3H, OCH₃)3.85(s, 3H, OCH₃) 4.45–4.60(m, 3H, H-2, H-4, H-5) 5.20(d, 1H, J=8.6Hz, NH) 6.57–7.44(m, 12H, arom) |

TABLE 3-continued

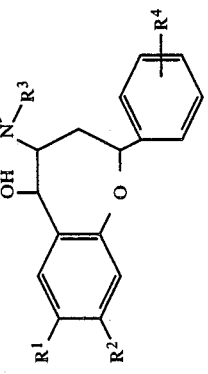

| Ref. Exp. No. (Comp. No.) | Substituent | | | | Melting Point (°C.) (Appearance) | IR Spectrum | NMR Spectrum |
|---|---|---|---|---|---|---|---|
| | $R^1$ | $R^2$ | $R^3$ | $R^4$ | | | |
| 22 (R22c) | H | H | 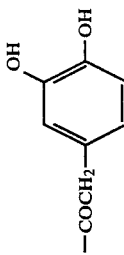—COCH$_2$—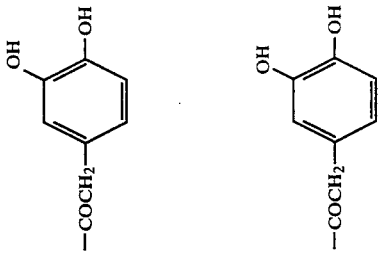 (OCH$_3$, OCH$_3$) | H | | 3380, 3050, 2900 1630, 1540, 1515 1450, 1260, 1220 1150, 1020, 950 750 | 2.07(m, 1H, H-3α)2.43(m, 1H, H-3β) 3.05(d, 1H, J=5.9Hz, OH) 3.48(s, 2H, COCH$_2$)3.82(s, 3H, OCH$_3$) 3.82(s, 3H, OCH$_3$)3.88(s, 3H, OCH$_3$) 4.27(m, 1H, H-4) 4.91–4.98(m, 2H, H-2, H-5) 5.83(d, 1H, J=7.3Hz, NH) 6.66–7.38(m, 1H, arom) 7.52(dd, 1H, J=1.3Hz, J=7.3Hz, H-6) |
| 23 (R23a) | H | H | —COCH$_2$—(OH, OH) | H | (amorphous) | 3500–2500, 1620 1500, 1440, 1220 1100, 1040, 740 | 2.20(m, 1H, H-3α)2.41(m, 1H, H-3β) 3.37(s, 2H, CH$_2$—Ar)4.39(m, 1H, H-4) 4.40(dd, 1H, J=11.9Hz, 2.0Hz, H-2) 4.50(d, H, H-5) 5.56(d, 1H, J=7.3Hz, NH) 6.37(dd, 1H, J=7.9Hz, 2.0Hz, H-6') 6.53(d, 1H, J=2.0Hz, H-2') 6.69(d, 1H, J=7.9Hz, H-5') 6.97(dd, 1H, J=9.2Hz, 1.3Hz, H-9) 7.12–7.40(m, 8H, arom) |
| 23 (R23b) | H | H | —COCH$_2$—(OH, OH) | H | (amorphous) | 3500–3000, 1640 1520, 1460, 1220 1040, 980, 750 695 | 2.05(m, 1H, H-3α)2.64(m, 1H, H-3β) 3.36(s, 2H, CH$_2$Ar)4.45(m, 1H, H-4) 4.61(m, 2H, H-2, H-5) 6.41(dd, 1H, J=7.9Hz, 2.0Hz, H-6') 6.59(d, 1H, J=2.0Hz, H-2') 6.67(d, 1H, J=7.9Hz, H-5') 6.97(d, 1H, J=7.9Hz, H-9) 7.03–7.14(m, 2H, H-7, H-8) 7.21–7.40(m, 6H, arom) |

TABLE 3-continued

| Ref. Exp. No. (Comp. No.) | Substituent | | | | Melting Point (°C.) (Appearance) | IR Spectrum | NMR Spectrum |
|---|---|---|---|---|---|---|---|
| | $R^1$ | $R^2$ | $R^3$ | $R^4$ | | | |
| 23 (R23c) | H | H | —COCH$_2$— (3,4-dihydroxyphenyl) | H | (amorphous) | 3500–2900, 1610 1510, 1480, 1340 1280, 1220, 1100 1030, 740, 680 | 2.00(m, 1H, H-3α)2.28(m, 1H, H-3β) 3.25 8s, 2H, CH$_2$Ar)4.15(m, 1H, H-4) 4.68(d, 1H, J=11.2Hz, H-2) 4.83(d, 1H, J=8.6Hz, H-5) 6.36(d, 1H, J=8.6Hz, NH) 6.48(d, 1H, J=7.9Hz, H-5') 6.61(m, 2H, H-2', H-6') 6.86(d, 2H, J=7.9Hz, H-9) 6.93(m, 1H, H-7)7.09(m, 1H, H-8) 7.13–7.24(m, 5H, arom) 7.34(m, 1H, H-6) |
| 24 (R24b) | H | H | —COCH$_2$— (3-pyridyl) | H | 198–200 | 3350, 3100, 1640 1560, 1480, 1350 1210, 1060, 950 720 | 2.04(m, 1H, H-3α)2.68(m, 1H, H-3β) 3.52(s, 2H, CH$_2$Ar)4.44(m, 1H, H-4) 4.80(d, 1H, J=6.6Hz, H-5) 4.91(dd, 1H, J=11.9Hz, 2.0Hz, H-2) 7.01(d, 1H, J=7.9Hz, H-9) 7.09(m, 1H, H-7)7.24–7.38(m, 7H, arom) 7.67(m, 1H, H-6) 8.39(d, 1H, J=2.0Hz, H-2') 8.44(dd, 1H, J=5.3Hz, 1.3Hz, H-6') |
| 24 (R24c) | H | H | —COCH$_2$— (3-pyridyl) | H | 193–194 | 3250, 3100, 1640 1560, 1480, 1220 1040, 950, 760 720, 700 | 2.13(m, 1H, H-3α) 2.54(ddd, 1H, J=14.5Hz, 4.6Hz, 2.6Hz, H-3β)3.49(s, 3H, CH$_2$Ar) 4.21(m, 1H, H-4)4.93(m, 2H, H-2, H-5) 7.98(dd, 1H, J=7.9Hz, 1.3Hz, H-9) 7.11–7.45(m, 8H, Ar) 7.49–7.55(m, 2H, H-5, H-5') 8.40(s, 1H, H-2') 8.46(d, 1H, H=4.6Hz, H-6') |

TABLE 4

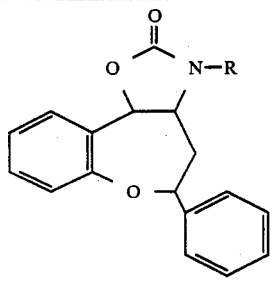

| Ref. Exp. No. (Comp. No.) | R | Melting Point (°C.) (Appearance) | IR Spectrum | NMR Spectrum |
|---|---|---|---|---|
| 25 (R25a) | H | | | 1.97–2.21 (m, 2H, H—3) 4.23 (m, 1H, H—4) 5.17 (dd, 1H, J=3.3 Hz, J=5.3 Hc, H—2) 5.95 (d, 1H, J=9.2 Hz, H—5) 6.49 (s, 1H, NH) 7.01–7.48 (m, 9H, arom) |
| 25 (R25b) | H | | 3230, 3000, 2850, 1760 1600, 1570, 1480, 1445 1350, 1310, 1230, 1040 1025, 1005, 755, 690 | 2.34 (m, 1H, H—3α) 2.78 (m, 1H, H—3β) 4.45 (m, 1H, H—4) 5.22–5.31 (m, 2H, H—2, 5) 5.81 (d, 1H, J=11.9 Hz, NH) 6.99–7.44 (m, 8H, arom) 7.57 (dd, 1H, J=1.3 Hz, J=7.8 Hz, H—6) |
| 25 (R25c) | H | 189.5–190 | 3220, 3130, 2880, 1770 1605, 1580, 1485, 1450 1320, 1240, 1020, 980 760, 700 | 2.34–2.54 (m, 2H, H—3) 3.84 (m, 1H, H—4) 4.67 (dd, 1H, J=2.0 Hz, J=10.6 Hz, H—2) 5.66 (d, 1H, J=10.6 Hz, H—5) 6.01 (s, 1H, NH) 7.07–7.54 (m, 9H, arom) |
| 25 (R25d) | H | | 3200, 3130, 2880, 1745 1600, 1580, 1480, 1445 1260, 1240, 1215, 1105 1030, 970, 760, 700 | 2.07–2.32 (m, 2H, H—3) 4.56 (m, 1H, H—4) 5.26 (m, 1H, H—2) 6.07 (d, 1H, J=9.2 Hz, H—5) 6.47 (dd, 1H, J=2.0 Hz, J=8.6 Hz, NH) 7.14–7.41 (m, 8H, arom) 7.54 (dd, 1H, J=2.0 Hz, J=8.6 Hz, H—6) |
| 26 (R26b) | —(CH₂)₂—C₆H₅ | | 3000, 2900, 1755, 1600 1470, 1450, 1400, 1350 1320, 1230, 1100, 1040 1020, 920, 750, 690 | 1.93 (m, 1H, H—3α) 2.52 (m, 1H, H—3β) 2.87 (t, 2H, J=7.3 Hz, H—2') 3.34–3.57 (m, 2H, H—1') 4.17 (m, 1H, H—4) 5.15 (dd, 1H, J=4.6 Hz, J=11.9 Hz, H—2) 5.57 (d, 1H, J=11.9 Hz, H—5) 6.95–7.43 (m, 13H, arom) 7.54 (d, d, 1H, J=1.3 Hz, J=7.9 Hz, H—6) |
| 26 (R26c) | —(CH₂)₂—C₆H₅ | | 3000, 2900, 2850, 1750 1600, 1570, 1480, 1440 1400, 1350, 1330, 1220 1150, 1020, 955, 760 690 | 1.98 (m, 1H, H—3α) 2.17 (m, 1H, H—3β) 2.88 (t, 2H, J=7.3 Hz, H—2') 3.38–3.57 (m, 3H, H—4, 1') 4.48 (dd, 1H, J=1.3 Hz, J=11.2 Hz, H—2) 5.44 (d, 1H, J=10.5 Hz, H—5) 7.02–7.46 (m, 13H, arom) 7.52 (m, 1H, H—6) |
| 27 (R27c) | —CH₃ | | 3060, 3040, 2890, 1770 1605, 1580, 1490, 1390 1360, 1240, 1230, 1040 1030, 770, 700 | 2.24–2.52 (m, 2H, H—3) 2.84 (s, 3H, N—CH₃) 3.49 (m, 1H, H—4) 4.68 (d, 1H, J=11.2 Hz, H—2) 5.53 (d, 1H, J=10.6 Hz, H—5) 7.06–7.54 (m, 9H, arom) |
| 27 (R27d) | —CH₃ | | 3020, 2920, 1760, 1600 1580, 1480, 1445, 1425 1400, 1255, 1215, 1170 1100, 1040, 930, 825 770, 750, 720, 690 | 2.03–2.26 (m, 2H, H—3) 2.82 (s, 3H, NCH₃) 4.28 (m, 1H, H—4) 5.26 (dd, 1H, J=3.9 Hz, J=11.9 Hz, H—2) 5.94 (d, 1H, J=9.9 Hz, H—5) 6.52 (m, 1H, arom) 7.15–7.40 (m, 7H, arom) 7.52 (m, 1H, H—6) |
| 28 (R28b) | —(CH₂)₃—C₆H₅ | | 3020, 2930, 2860, 1760 1600, 1580, 1485, 1455 1410, 1360, 1320, 1235 1100, 1040, 1030, 920 750, 700 | 1.79–1.94 (m, 2H, H—2') 2.17 (m, 1H, H—3α) 2.56–2.74 (m, 3H, H—3β, 3) 3.17 (m, 1H, H—1'α) 3.41 (m, 1H, H—1'β) 4.20 (m, 1H, H—4) 5.21 (m, 1H, H—2) 5.60 (d, 1H, J=11.9 Hz, H—5) 6.95–7.42 (m, 13H, arom) 1.54 (d, 1H, J=7.9 Hz, H—6) |

TABLE 4-continued

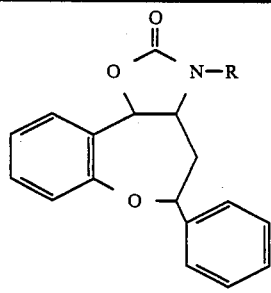

| Ref. Exp. No. (Comp. No.) | R | Melting Point (°C.) (Appearance) | IR Spectrum | NMR Spectrum |
|---|---|---|---|---|
| 28 (R28c) | $-(CH_2)_3-\phenyl$ | | 3000, 2900, 2850, 1650 1600, 1570, 1480, 1440 1400, 1350, 1320, 1220 1020, 960, 760, 685 | 1.82-1.93 (m, 2H, H—2') 2.22-2.36 (m, 2H, H—3) 2.65 (dd, 2H, J=6.6 Hz, J=8.6 Hz, H—3') 3.18-3.41 (m, 2H, H—1') 3.57 (m, 1H, H—4) 4.63 (dd, 1H, J=2.6 Hz, J=10.6 Hz, H—2) 5.50 (d, 1H, J=10.6 Hz, H—5) 7.05-7.48 (m, 13H, arom) 7.53 (m, 1H, H—6) |
| 29 (R29c) | $-(CH_2)_2-\pyridyl$ | | | 1.98 (m, 1H, H—3α) 2.39 (m, 1H, H—3β) 3.06 (t, 2H, J=7.2 Hz, H—1') 3.54 (m, 1H, H—4) 3.60-3.74 (m, 2H, H—2') 4.53 (dd, 1H, J=1.3 Hz, J=11.2 Hz, H—2 or 5) 5.45 (d, 1H, J=11.2 Hz, H—2 or 5) 7.03-7.63 (m, 12H, arom) 8.43 (d, 1H, J=3.9 Hz, H—3") |

FORMULATION 1

Capsule

| Ingredients for one capsule | |
|---|---|
| (1) Compound 1c (Example 1) | 10 mg |
| (2) Lactose | 59.5 mg |
| (3) Corn starch | 80 mg |
| (4) Soft silica anhydride | 0.5 mg |
| Total | 150 mg |

Procedure

The above-mentioned components were thoroughly mixed and then filled in a gelatin capsule.

FORMULATION 2

Tablet

| Ingredients for one tablet | |
|---|---|
| (1) Compound 1c of Example 1 | 10 mg |
| (2) Lactose | 59 mg |
| (3) Corn starch | 70 mg |
| (4) Corn starch paste | 10 mg |
| (5) Magnesium stearate | 1 mg |

Procedure

The above-mentioned components were mixed and pressed to a tablet form according to a conventional procedure.

Biological test

Hypoglycemic activity, hypotensive activity, and platelet coagulation inhibiting activity of the present compounds were tested as follow.

1. Hypoglycemic activity

Male ddY mice aged five to six weeks were starved for 24 hours, and test compound was then administered, i.e., in the form of CMC suspension. After 30 minutes from the administration, a blood sample was obtained from tale, the sample was immediately centrifuged, and the glucose concentration in serum was determined by a glucose oxidase method (using a commercially available kit).

2. Hypotensive activity

Twenty-week aged male spontaneous hypertensive rats (SHR) were anesthetized with ether, and a cannula was inserted into the aorta. After one day, the cannula was connected to a pressure transducer, and the blood pressure was continuously measured under non-arrest and non-anesthetic conditions. A test compound was orally administered in the form of a 0.5% CMC suspension after over night-starvation of the SHR.

3. Platelet coagulation inhibiting activity

Healthy men, and male white rabbits having a body weight of 4 kg, were used. Blood samples were obtained from the elbow vein in case of the men, or from an ear artery in the case of the white rabbits, and 0.31% or 0.38% citric acid was added to each sample. The samples were centrifuged to obtain platelet rich plasma (PRP), which were then subjected to measurement of the blood platelet coagulation ability. ADP, arachidonic acid, collagen, platelet activating factor (PAF), epinephrine and $Ca^{++}$ ionophore A-23187 were used as the coagulation inducer. The test compound was dissolved in dimethylsulfoxide, and the solution was added to the PRP for administration.

Result

Among the compounds of the present invention, compounds 1(1b, 1c, 1d), 4(4c), 6(6c), 7(7b, 7c), 8(8c), 10(10a, 10c) 11(11c), 13(13a, 13b, 13c), 14(14c), 16(16c), 17(17b, 17c), 18(18c), 20(20c), 21(21c), 25(25c), 26(26c), 27(27c), 28(28c), 31(31c), and 32(32c) showed a significant hypoglycemic activity at a dose of 10 mg/kg P.O. Further, compound 1(1c) showed a significant hypoglycemic activity at a dose of 10 mg/kg as well as a hypotensive activity and platelet coagulation inhibiting activity.

We claim:

1. A 2-phenylbenzoxepin derivative represented by the following formula (I):

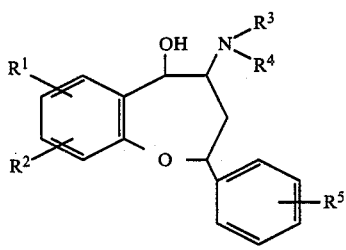

wherein $R^1$ and $R^2$ independently represent a hydrogen atom, a halogen atom, hydroxyl group, methyl group or methoxy group;

$R^3$ and $R^4$ independently represent a hydrogen atom, lower alkyl group or the group $-(CH_2)_n-Y$ wherein n represents an integer of 1 to 5, and Y represents a pyridyl, pyrimidyl, furyl, thenyl or phenyl group which are unsubstituted or substituted with one to three members of the group consisting of $CH_3$, $OCH_3$, OH and halogen; or $R^3$ and $R^4$, together with a nitrogen atom to which they are bonded, form pyrolidine ring, piperidine ring, piperazine ring, morpholine ring or thiomorpholine ring; and $R^5$ represents a hydrogen atom, halogen atom, $CH_3$, $OCH_3$, $CF_3$, $CH_2OH$ or $COOR^6$ group; wherein $R^6$ represents a lower alkyl group;

and pharmaceutically acceptable acid addition salts thereof.

2. A 2-phenylbenzoxepin derivative according to claim 1, wherein the lower alkyl group $R^3$ and $R^4$ is selected from the group consisting of methyl, ethyl, propyl, butyl, pentyl and hexyl.

3. A pharmaceutical composition which acts as a hypoglycemic agent comprising a sufficient amount of a 2-phenylbenzoxepin derivative according to claim 1 to provide a hypoglycemic response or pharmaceutically acceptable acid addition salt thereof and a pharmaceutically acceptable carrier.

* * * * *